United States Patent
Steingrimsson et al.

(10) Patent No.: US 11,710,539 B2
(45) Date of Patent: Jul. 25, 2023

(54) PREDICTIVE TEST FOR MELANOMA PATIENT BENEFIT FROM INTERLEUKIN-2 (IL2) THERAPY

(71) Applicant: Biodesix, Inc., Boulder, CO (US)

(72) Inventors: Arni Steingrimsson, Steamboat Springs, CO (US); Carlos Oliveira, Steamboat Springs, CO (US); Krista Meyer, Steamboat Springs, CO (US); Joanna Röder, Steamboat Springs, CO (US); Heinrich Röder, Steamboat Springs, CO (US)

(73) Assignee: BIODESIX, INC., Boulder, CO (US)

( * ) Notice: Subject to any disclaimer, the term of this patent is extended or adjusted under 35 U.S.C. 154(b) by 1203 days.

(21) Appl. No.: 16/070,603

(22) PCT Filed: Jan. 18, 2017

(86) PCT No.: PCT/US2017/013920
§ 371 (c)(1),
(2) Date: Jul. 17, 2018

(87) PCT Pub. No.: WO2017/136139
PCT Pub. Date: Aug. 10, 2017

(65) Prior Publication Data
US 2019/0018929 A1  Jan. 17, 2019

Related U.S. Application Data

(60) Provisional application No. 62/369,289, filed on Aug. 1, 2016, provisional application No. 62/289,587, filed on Feb. 1, 2016.

(51) Int. Cl.
| | |
|---|---|
| *G01N 33/48* | (2006.01) |
| *G16B 40/20* | (2019.01) |
| *G16B 40/00* | (2019.01) |
| *G16H 50/70* | (2018.01) |
| *C12Q 1/68* | (2018.01) |
| *A61K 39/00* | (2006.01) |
| *G16H 20/17* | (2018.01) |
| *G01N 33/68* | (2006.01) |
| *H01J 49/00* | (2006.01) |

(52) U.S. Cl.
CPC .............. *G16B 40/20* (2019.02); *A61K 39/00* (2013.01); *C12Q 1/68* (2013.01); *G01N 33/6848* (2013.01); *G16B 40/00* (2019.02); *G16H 20/17* (2018.01); *G16H 50/70* (2018.01); *H01J 49/0036* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 7,736,905 B2 | 6/2010 | Roder et al. |
| 7,858,389 B2 | 12/2010 | Roder et al. |
| 7,858,390 B2 | 12/2010 | Roder et al. |
| 7,867,775 B2 | 1/2011 | Roder et al. |
| 7,879,620 B2 | 2/2011 | Roder et al. |
| 7,906,342 B2 | 3/2011 | Roeder et al. |
| 8,024,282 B2 | 9/2011 | Tsypin et al. |
| 8,097,469 B2 | 1/2012 | Roder et al. |
| 8,119,417 B2 | 2/2012 | Roeder et al. |
| 8,119,418 B2 | 2/2012 | Roeder et al. |
| 8,467,988 B1 | 6/2013 | Roder et al. |
| 8,586,379 B2 | 11/2013 | Roeder et al. |
| 8,586,380 B2 | 11/2013 | Roeder et al. |
| 8,718,996 B2 | 5/2014 | Brauns et al. |
| 8,914,238 B2 | 12/2014 | Roder et al. |
| 9,152,758 B2 | 10/2015 | Roder et al. |
| 9,211,314 B2 | 12/2015 | Roder et al. |
| 9,254,120 B2 | 2/2016 | Roeder et al. |

(Continued)

FOREIGN PATENT DOCUMENTS

| | | |
|---|---|---|
| CN | 103339509 A | 10/2013 |
| CN | 103384827 A | 11/2013 |
| CN | 103842030 A | 6/2014 |
| CN | 104470949 A | 3/2015 |
| CN | 104685360 A | 6/2015 |
| CN | 105512669 A | 4/2016 |
| CN | 105745659 A | 7/2016 |
| EP | 1043676 A2 | 10/2000 |
| EP | 2241335 A1 | 10/2010 |
| WO | 2010085234 A1 | 7/2010 |

(Continued)

OTHER PUBLICATIONS

Hardesty, William M., et al. "Protein signatures for survival and recurrence in metastatic melanoma." Journal of proteomics vol. 74 (2011) pp. 1002-1014.*

(Continued)

*Primary Examiner* — Anna Skibinsky
(74) *Attorney, Agent, or Firm* — Lathrop GPM LLP; Lisa Hillman

(57) ABSTRACT

A method is disclosed for predicting in advance whether a melanoma patient is likely to benefit from high dose IL2 therapy in treatment of the cancer. The method makes use of mass spectrometry data obtained from a blood-based sample of the patient and a computer configured as a classifier and making use of a reference set of mass spectral data obtained from a development set of blood-based samples from other melanoma patients. A variety of classifiers for making this prediction are disclosed, including a classifier developed from a set of blood-based samples obtained from melanoma patients treated with high dose IL2 as well as melanoma patients treated with an anti-PD-1 immunotherapy drug. The classifiers developed from anti-PD-1 and IL2 patient sample cohorts can also be used in combination to guide treatment of a melanoma patient.

4 Claims, 17 Drawing Sheets

(56) References Cited

U.S. PATENT DOCUMENTS

| | | | |
|---|---|---|---|
| 9,279,798 | B2 | 3/2016 | Roder et al. |
| 9,477,906 | B2 | 10/2016 | Roder et al. |
| 9,563,744 | B1 | 2/2017 | Roder et al. |
| 9,606,101 | B2 | 3/2017 | Roder et al. |
| 9,724,413 | B2 | 8/2017 | Maecker et al. |
| 9,779,204 | B2 | 10/2017 | Roder et al. |
| 9,824,182 | B2 | 11/2017 | Roder et al. |
| 10,007,766 | B2 | 6/2018 | Roder et al. |
| 10,037,874 | B2 | 7/2018 | Roder et al. |
| 10,217,620 | B2 | 2/2019 | Roder et al. |
| 10,489,550 | B2 | 11/2019 | Roder et al. |
| 10,713,590 | B2 | 7/2020 | Roder et al. |
| 2003/0225526 | A1 | 12/2003 | Golub et al. |
| 2005/0149269 | A1 | 7/2005 | Thomas et al. |
| 2007/0231921 | A1 | 10/2007 | Roder et al. |
| 2007/0269804 | A1 | 11/2007 | Liew et al. |
| 2008/0032299 | A1 | 2/2008 | Burczynski et al. |
| 2008/0306898 | A1 | 12/2008 | Tsypin et al. |
| 2010/0174492 | A1 | 7/2010 | Roder |
| 2010/0240546 | A1 | 9/2010 | Lo |
| 2011/0208433 | A1 | 8/2011 | Grigorieva et al. |
| 2011/0271358 | A1 | 11/2011 | Freeman et al. |
| 2013/0131996 | A1 | 5/2013 | Roder et al. |
| 2013/0344111 | A1 | 12/2013 | Roder et al. |
| 2014/0044673 | A1 | 2/2014 | Caprioli |
| 2014/0200825 | A1 | 7/2014 | Roder et al. |
| 2014/0341902 | A1 | 11/2014 | Maecker et al. |
| 2015/0071910 | A1 | 3/2015 | Kowanetz et al. |
| 2015/0102216 | A1 | 4/2015 | Roder et al. |
| 2015/0125463 | A1 | 5/2015 | Cogswell et al. |
| 2015/0285817 | A1 | 10/2015 | Roder et al. |
| 2016/0019342 | A1 | 1/2016 | Roder et al. |
| 2016/0098514 | A1 | 4/2016 | Roder et al. |
| 2016/0163522 | A1 | 6/2016 | Roder et al. |
| 2016/0018410 | A1 | 10/2016 | Roder et al. |
| 2016/0298198 | A1* | 10/2016 | Hernando-Monge ........................ A61K 31/506 |
| 2016/0299146 | A1 | 10/2016 | Garraway et al. |
| 2017/0039345 | A1 | 2/2017 | Röder et al. |
| 2017/0271136 | A1 | 9/2017 | Roder et al. |
| 2018/0021431 | A1 | 1/2018 | Maecker et al. |
| 2018/0027249 | A1 | 9/2018 | Roder et al. |
| 2019/0035364 | A1 | 11/2019 | Oliveira et al. |

FOREIGN PATENT DOCUMENTS

| | | | |
|---|---|---|---|
| WO | 2012069462 | A1 | 5/2012 |
| WO | 2014003853 | A1 | 1/2014 |
| WO | 2014007859 | A1 | 1/2014 |
| WO | 2014055543 | A2 | 4/2014 |
| WO | 2014149629 | A1 | 9/2014 |
| WO | 2015039021 | A2 | 3/2015 |
| WO | 2015/153991 | A1 | 10/2015 |
| WO | 2015153991 | A1 | 10/2015 |
| WO | 2015157109 | A1 | 10/2015 |
| WO | 2015176033 | A1 | 11/2015 |
| WO | 2016049385 | A1 | 3/2016 |
| WO | 2016054031 | A1 | 4/2016 |
| WO | 2016089553 | A1 | 6/2016 |
| WO | 2017011439 | A1 | 1/2017 |

OTHER PUBLICATIONS

Serrano.Academy "A friendly introduction to Recurrent Neural Networks" Aug. 18, 2017 [online], [retrieved on Jul. 23, 2022]. Retrieved from the Internet <URL: https://www.youtube.com/watch?v=UNmqTiOnRfg>.*

Thales Sehn Korting "How kNN algorithm works." Feb. 18, 2014 [online], [retrieved on Nov. 18, 2022]. Retrieved from the Internet <URL:https://www.youtube.com/watch?v=UqYde-LULfs>.*

Althammer et al, "Biomarkers and Immune Monitoring", Journal for Immunotherapy of Caner, vol. 4, No. 91, pp. 223-242, Dec. 8, 2016.

Biodesix's Diagnostic Cortex™ Platform Used in Three Studies Presented at SITC, Nov. 15, 2016, Retrieved from the Internet Oct. 26, 2020, URL: https://www.biodesix.com/press-releases/biodesixs-diagnostic-cortex-platform-used-three-studies-presented-sitc.

Blanco et al, "Feature selection in Bayesian classifiers for the prognosis of survival of cirrhotic patients treated with TIPS", Journal of Biomedical Informatics, vol. 38, pp. 376-388, (2005).

Bruno et al, "Overexpression of PD-1 and PD-L 1 in Penal Cell Carcinoma is associated with poor prognosis in metastatic patients treated with subtinib", Annals of Oncology, vol. 26, No. 2, Annual Meeting Poster, (2015).

Carvajal-Hausdorf et al, "Quantitative Measurement of Cancer Tissue Biomarkers in the Lab and in the Clinic", Lab Invest, vol. 95, No. 4, pp. 385-396, (2015).

Girosi et al, "Regularization Theory and Neural Architectures", Neural Computation, vol. 7, pp. 219-269, (1995).

Grivennikov et al, "Immunity, inflammation, and cancer", Cell, vol. 140, pp. 883-899, (2010).

Gunn et al, "Opposing roles for complement component C5a in tumor progression and the tumor microenvironment", J Immunol, vol. 189, pp. 2985-2994, (2012).

International Search Report and Written Opinion for PCT Application No. PCT/US2016/041860 dated Oct. 6, 2016.

International Search Report for PCT application No. PCT/US17/13920, dated May 19, 2017.

International Search Report for PCT application No. PCT/US2018/12564, dated Mar. 26, 2018.

International Search Report for PCT application No. PCT/US2019/021641, dated Jul. 3, 2019, 7 pages.

Janelle et al, "Role of the complement system in NK cell-mediated antitumor T-cell responses", Oncoimmunology, vol. 3, e27897, (2014).

Janelle et al, "Transient complement inhibition promotes a tumor-specific immune response through the implication of natural killer cells", Cancer Immunol Res, vol. 2, pp. 200-206, (2014).

Kani et al, "Quantitative Proteomic profiling identifies protein correlates to EGFR kinase inhibition", Mol Cancer Ther., Vo. 11, No. 5, pp. 1071-1081, (2012).

Karpievitch et al, "Liquid Chromatography Mass Spectrometry-Based Proteomics: Biological and Technological Aspects", Ann Appl Stat., vol. 4, No. 4, pp. 1797-1823, (2010).

Kennedy-Crispin et al, "Human keratinocytes' response to injury upregulates CCl20 and other genes linking innate and adaptive immunity", J Invest Dermatol., vol. 132, No. 1, pp. 105-113, (2012).

Larkin et al, "Combined Nivolumab and Ipilimumab or Monotherapy in Untreated Melanoma", The New England Journal of Medicine, vol. 373, No. 1, pp. 23-34, (2015).

Lundqvist et al, "Adoptive Cellular Therapy", Journal for Immunotherapy of Cancer, vol. 4, No. 82, pp. 1-221, Nov. 16, 2016.

Mantovani et al, "Cancer-related inflammation", Nature, vol. 454, pp. 436-444, (2008).

Markiewski et al, "Modulation of the antitumor immune response by complement", Natl Immunol, vol. 9, pp. 1225-1235, (2008).

Mathern et al, "Molecules Great and Small: The Complement System", Clin J Am Soc Nephrol, vol. 10, pp. 1636-1650, (2015).

McDeromott et al, "Durable benefit and the potential for long-term survival with immunotherapy in advanced melanoma", Cancer Treatment, vol. 40, No. 9, pp. 1056-1064, Apr. 8, 2014.

Mootha et al, "PGC-1 α-responsive genes involved in oxidative phosphorylation are coordinately downregulated in human diabetes", Nat Genet., vol. 34, No. 3, pp. 267-273, (2003).

Pearson et al, J. Clinical Oncology, vol. 34, No. 15, Meeting Abstract, May 2016.

Pio et al, "The role of complement in tumor growth", Adv Exp Med Biol, vol. 772, pp. 229-262, (2014).

Porta et al, "Cellular and molecular pathways linking inflammation and cancer", Immunobiology, vol. 214, pp. 461-777, (2009).

Postow et al, "Peripheral and tumor immune correlates in patients with advanced melanoma treated with nivolumab (aniti-PD-1, BMS-936558, ONO-4538) monotherapy or in combination with ipilimumab", Journal of Translational Medicine, vol. 12, No. 1, pp. 1-2, (2014).

(56) References Cited

OTHER PUBLICATIONS

Qi et al, "Advances in the study of serum tumor markers of lung cancer", Journal of Cancer and Therapeutics, vol. 10, No. 2, pp. C95-C101, (2014).
Redman et al, "Advances in immunotherapy for melanoma", BNC Medicine, vol. 14, No. 1, pp. 1-11, (2016).
Romano et al, "The therapeutic promise of disrupting the PD-1/PD-L1 immune checkpoint in cancer: unleashing the CD8 cell mediated anti-tumor activity results in significant, unprecedented clinical efficacy in various solid tumors", J. ImmunoTher. Can., vol. 3, No. 15, pp. 1-5, (2015).
Shrivastava, "Improving Neural Networks with Dropout", Master's Thesis, Graduate Department of Computer Science, University of Toronto, (2013).
Subramanian et al, "Gene set enrichment analysis: A knowledge-based approach for interpreting genome-wide expression profiles", Proc Natl Acad Sci USA, vol. 102, No. 43, pp. 15545-15550, (2005).
Taguchi et al, "Mass Spectrometry to Classify Non-Small-Cell Lung Cancer Patients for Clinical Outcome after Treatment with Epidermal Growth Factor Receptor Tyrosine Kinase Inhibitors: A Multicohort Cross-Institutional Study", UNCI Journal of the National Cancer Institute, vol. 99, No. 11, pp. 838-846, (2007).
Taneja et al, "Markers of Small Cell Lung Cancer", World Journal of Surgical Oncology, vol. 2, No. 10, 5 pages, May 5, 2004.
Tibshirani, "Regression shrinkage and selection via the lasso", J. Royal. Statist. Soc B, vol. 58, No. 1, pp. 267-288, (1996).
Tikhonov, "On the stability of inverse problems", Doklady Akademii Nauk SSSR, vol. 39, No. 5, pp. 195-198, (1943).
Vadrevu et al, "Complement c5a receptor facilities cancer metastasis by altering T-cell responses in the metastatic niche", Cancer Res, vol. 74, pp. 3454-3565, (2014).
Vu et al, "RAC1 P29S regulates PD-L1 expression in melanoma", Pigment Cell Melanoma Res., vol. 28, No. 5, pp. 590-598, (2015).
Weber et al, "Pre-treatment selection for nivolumab benefit based on serum mass spectra", Journal for Immunotherapy of Cancer, No. 3, pp. 1-2, Nov. 4, 2015.
Weber et al, "A Serum Protein Signature Associated with Outcome After Anti-PD-1 Therapy in Metastatic Melanoma", ACCR Special Conference on Tumor Immunology and Immunotherapy, Boston, MA, vol. 6, No. 1, pp. 79-86, (2016).
Weber et al, "A test identifying advanced melanoma patients with long survival outcomes on nivolumab shows potential for selection for benefit from combination checkpoint blockade", 31st Annual Meeting and Associated Programs of the Society for Immunotherapy of Cancer, vol. 4, No. 82, (2016).
Weber et al, "Safety, Efficacy, Biomarkers of Nivoluamb With Vaccine in Ipilimumab or -Naïve Melanoma", J. Clin. Oncol., vol. 31, pp. 4311-4318, (2013).
Written Opinion of the International Searching Authority for PCT/US219/021641, dated Jul. 3, 2019, 12 pages.
Zang et al, "Progress in immunotherapy of melanoma", Chinese Journal of Cancer Biotherapy, vol. 20, No. 3, Jun. 30, 2013.
Zhang et al, "A Protective Role for C5a in the Development of Allergic Asthma Associated with Altered Levels of B7-H1 and B7-DC on Plasmacytoid Dendritic Cells", J. Immunol., vol. 182, pp. 5123-5130, (2009).
Zhang et al, "Simultaneous blocking of PD-1 and CTLA-4 increases in T cell infiltration in melanoma and reduces the number of Treg and bone-marrow derived suppressor cells", Progress in Physiological Sciences, vol. 43, No. 2, Dec. 31, 2012.
International Search Report for corresponding PCT application No. PCT/US17/13920, dated May 19, 2017.

\* cited by examiner

PFS

OS

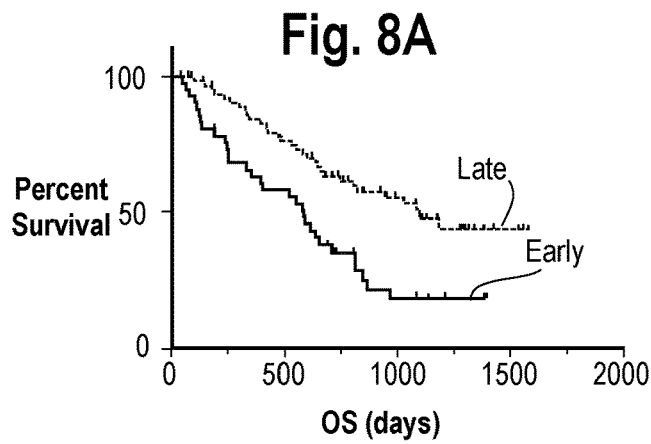
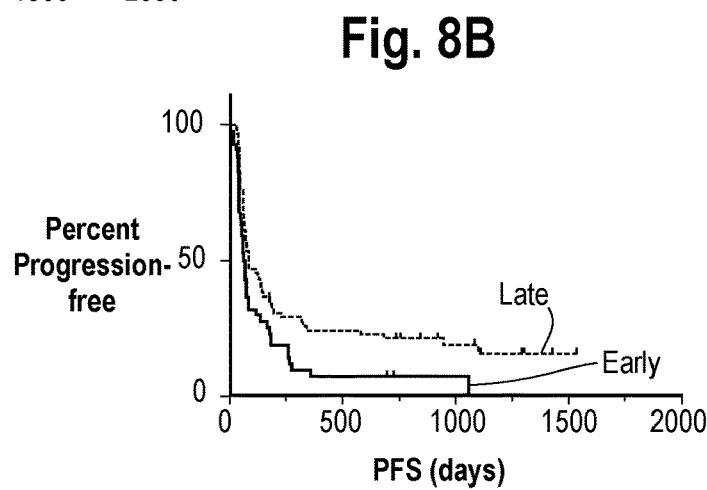
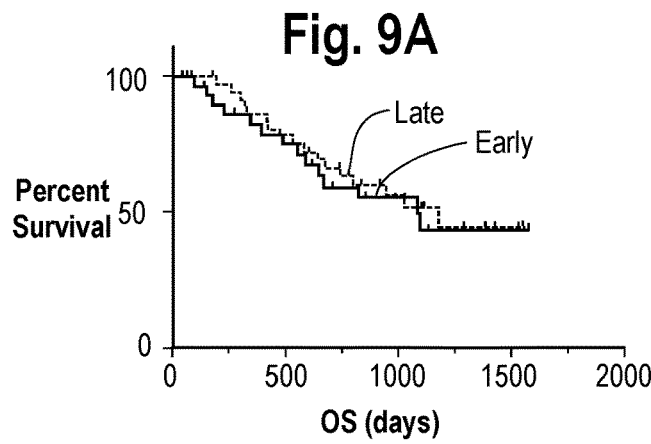
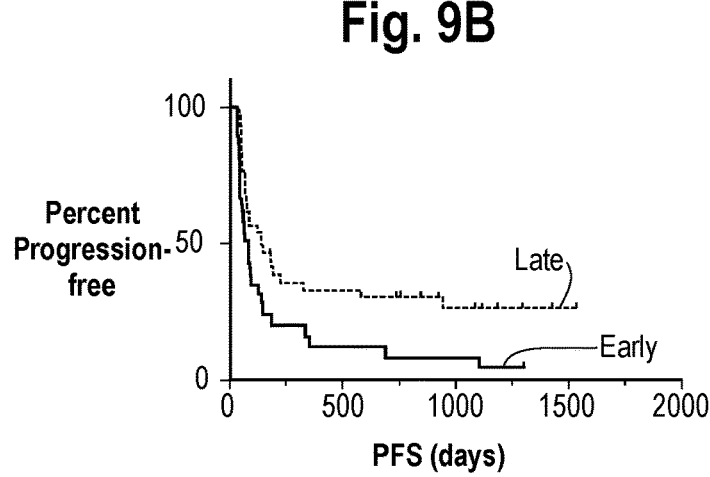

PREDICTIVE TEST FOR MELANOMA PATIENT BENEFIT FROM INTERLEUKIN-2 (IL2) THERAPY

PRIORITY

This application claims priority benefits to U.S. provisional application Ser. No. 62/289,587 filed Feb. 1, 2016, and U.S. provisional application Ser. No. 62/369,289 filed Aug. 1, 2016. The content of each of the above-referenced applications is incorporated by reference herein.

FIELD

This invention relates to a method for predicting in advance of treatment whether a melanoma patient is likely to benefit from administration of high dose IL2 therapy in treatment of the cancer.

BACKGROUND

Interleukin-2 (IL2) is a cytokine signaling molecule in the immune system. It is a protein that regulates the activities of white blood cells (leukocytes, often lymphocytes) that are responsible for immunity. There are different dosages of IL2 across the United States and across the world being used to treat patients. The efficiency and side effects of different dosages is often a point of disagreement. Usually, in the U.S., the higher dosage option is used, depending on the cancer, response to treatment, and general health of the patient. Patients are typically given the high dosages for five consecutive days, three times a day, for fifteen minutes. The patient is given approximately 10 days to recover between treatment dosages. IL2 is delivered intravenously for this type of dosing, and administration at hospital is generally required to enable proper monitoring of side effects.

High dose IL2 therapy has been approved for the treatment of renal cell carcinoma and melanoma. It is the only immunotherapy that offers the chance of a cure—a lasting complete response—to around 10% of patients. Both in metastatic renal cell carcinoma (R Fisher, S Rosenberg, G Fyfe, *Long-term survival update for high-dose recombinant interleukin-2 in patients with renal cell carcinoma.* Cancer J Sci Am. 2000 February; 6 Suppl 1:S55-7) and in metastatic melanoma (M Atkins, M Lotze, J Dutcher, et al., *High-dose recombinant interleukin 2 therapy for patients with metastatic melanoma: analysis of 270 patients treated between 1985 and 1993.* J Clin Oncol 1999 July; 17(7):2105-16), a proportion of patients experience durable compete responses with little or no long term toxicity from treatment. However, high dose IL2 therapy requires hospitalization for 1-2 weeks during each of (usually) two treatment courses. Close monitoring by an experienced medical team is required during this period due to the likelihood of severe side effects from capillary leak syndrome. These are short-term, however, with patients recovering to pre-treatment status within about 3 days of the end of IL2 administration (see, e.g., A Amin and R White Jr, *High-dose interleukin-2: is it still indicated for melanoma and RCC in an era of targeted therapies.* Oncology (Williston Park). 2013 July; 27(7):680-91).

There have been efforts to find pre-treatment tests or biomarkers able to predict which patients will experience these durable responses from IL2 therapy (see, e.g. M Sabatino, S Kim-Schulze, M Panelli, et al., *Serum Vascular Endothelial Growth Factor and Fibronectin Predict Clinical Response to High-Dose Interleukin-2 Therapy*, J Clin Oncol. 2009 Jun. 2; 27(16) 2645-2651), but, as yet, none have passed adequate validation. The "SELECT" trial, for example, designed to assess the ability of a test integrating IHC staining for carbonic anhydrase-9 with histological sub-classification to predict response to IL2 therapy for treatment of patients with metastatic renal cell carcinoma (D McDermott, S Cheng, S Signoretti, et al., *The High-Dose Aldesleukin "Select" Trial: A Trial to Prospectively Validate Predictive Models of Response to Treatment in Patients with Metastatic Renal Cell Carcinoma.* Clin Cancer Res. 2015 Feb. 1; 21(3):561-8.) did not validate this test as useful for predicting response. While it may be possible to identify small proportions of patients (around 10% or less), based on non-clear cell histology or baseline clinical and pathological characteristics (e.g., University of California Los Angeles Survival After Nephrectomy and Immunotherapy Score—UCLA SANI Score, ibid) who will not respond to IL2 therapy, little progress has been made in providing a clinically useful test for patient selection for this treatment. Some earlier observations, however, may be of interest. In particular, acute response proteins or regulators of acute response may serve as important dynamic markers of pre-treatment prognosis and predictors of response in the course of treatment. It was shown that non-responders have high pre-treatment levels of C-reactive protein (CRP) and interleukin 6 (IL-6). In contrast, patients with good responses, have significantly lower levels of these proteins at baseline, and develop high circulating levels of IL-6 and CRP at different time intervals during the infusion (Broom J, Heys S D, Whiting P H, Park K G, Strachan A, Rothnie I, Franks C R, Eremin O. *Interleukin 2 therapy in cancer: identification of responders.* Br J Cancer. 1992 December; 66(6): 1185-7; Deehan D J, Heys S D, Simpson W G, Broom J, Franks C, Eremin O. *In vivo cytokine production and recombinant interleukin 2 immunotherapy: an insight into the possible mechanisms underlying clinical responses.* Br J Cancer. 1994 June; 69(6):1130-5.)

The lack of a test able to select patients for IL2 therapy has become more of a problem with the advent of new effective immunotherapy options, such as nivolumab and pembrolizumab and the combination of ipilimumab and nivolumab in melanoma and nivolumab in renal cell carcinoma, all recently approved by the FDA. These checkpoint inhibitor therapies, while not producing the cures characteristics of IL2, do produce extremely durable responses, at least able to turn cancer into a chronic condition for some patients. Hence, there is now an urgent need for tests to help physicians and patients choose between or sequence IL2 and these other immunotherapeutic options.

SUMMARY

In a first aspect, a method is disclosed for predicting in advance whether a melanoma patient is likely to benefit from high dose IL2 therapy in treatment of the cancer. The method includes the steps of:

a) performing mass spectrometry on a blood-based sample of the patient and obtaining mass spectrometry data of the sample;

b) performing a classification of the mass spectrometry data with the aid of a computer implementing a classifier, wherein the classifier is developed from a development set of samples from melanoma patients treated with the high dose IL2 therapy and consists of a hierarchical combination of classifiers 1 and 2. Classifier 1 is developed from the development set of samples and a set of mass spectral features identified as being associated with an acute response biological function and generates either an Early class label and a Late class label, or the equivalent. Classifier 2 is developed from a subset of samples in the development set which are classified as Late by classifier 1. Classifier 2 also generates an Early class label and a Late class label or the equivalent. If the sample from the patient is classified as Late by both classifier 1 and classifier 2, the patient is predicted to have a greater likelihood of benefit from the high dose IL2 therapy as compared to if the sample from the patient is classified as Early by either classifier 1 or classifier 2.

In one embodiment classifier 1 and classifier 2 use the features for performing classification of the sample recited in Table 33.

It is noted below that classifier 2 alone performs similarly to the hierarchical combination of classifiers 1 and 2. Accordingly, in another aspect a method for predicting in advance whether a melanoma patient is likely to benefit from high dose IL2 therapy in treatment of the cancer is disclosed comprising the steps of: a) performing mass spectrometry on a blood-based sample of the patient and obtaining mass spectrometry data of the sample; b) performing a classification of the mass spectrometry data with the aid of a computer implementing a classifier 2, wherein the classifier 2 is developed from a subset of a development set of samples from melanoma patients treated with the high dose IL2 therapy which have been classified as Late or the equivalent by a classifier 1 using a set of mass spectral features identified as being associated with an acute response biological function; wherein if the sample from the patient is classified as Late or the equivalent by classifier 2 the patient is predicted to have a greater likelihood of benefit from the high dose IL2 therapy as compared to if the sample from the patient is classified by classifier 2 as Early or the equivalent.

In other aspects, a computer configured as a classifier for predicting melanoma patient benefit from high dose IL2 and a testing system for conducting the tests of this disclosure are also considered inventive aspects.

BRIEF DESCRIPTION OF THE DRAWINGS

FIGS. 8A and 8B illustrate Kaplan-Meier plots of OS (FIG. 8A) and PFS (FIG. 8B) by classification groups Early and Late produced by the Classifier 1 described below.

FIGS. 9A and 9B illustrate Kaplan-Meier plots of OS (FIG. 9A) and PFS (FIG. 9B) by classification groups Early and Late produced by the Classifier 2 described below when classifying the 70 samples which were classified as Late by Classifier 1.

DETAILED DESCRIPTION

This document will initially describe a set of blood-based samples obtained from a population of melanoma patients in advance of treatment and the generation and processing of mass spectral data which is used for classifier development. Later, in the context of FIG. 7, we describe the development of a computer-implemented classifier from this mass spectral data which is able to predict whether a melanoma patient is likely to benefit from high dose IL2 in treatment of the cancer. We further illustrate the results of the classifiers developed from the FIG. 7 procedure. A laboratory testing environment for conducting the test is also described in conjunction with FIG. 13. We later describe the application of two classifiers from our U.S. provisional application Ser. No. 62/289,587 filed Feb. 1, 2016 on the IL2 sample set as well as the IL2 classifier performance on the 119 melanoma patient samples used to develop the anti-PD-1 classifier of the U.S. provisional application Ser. No. 62/289,587 filed Feb. 1, 2016.

Our method for obtaining data for use in classifier generation and making predictive tests uses matrix assisted laser desorption and ionization time of flight (MALDI-TOF) mass spectrometry. Preferred embodiments use the so-called Deep MALDI methods described in U.S. Pat. No. 9,279,798, the content of which is incorporated by reference herein.

A. Samples, Mass Spectral Data Acquisition and Pre-Processing of Spectra

Patient Samples

One hundred and fourteen blood-based (serum) samples were available with good quality mass spectra and associated clinical data. No baseline clinical data was available for this patient cohort. The samples were acquired from melanoma patients pre-treatment with high dose IL2.

Figure 1A:
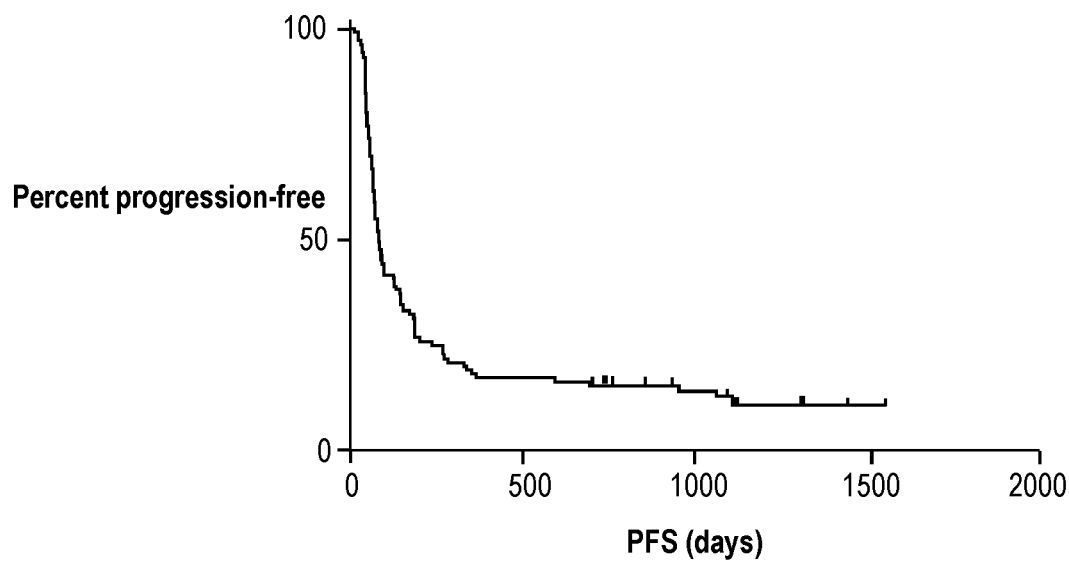
FIGS. 1A and 1B illustrate Kaplan-Meier plots for progression-free survival (PFS) (FIG. 1A) and overall survival (OS) (FIG. 1B) for the cohort of 114 patients with baseline samples and acquired spectra which were used to develop the classifiers of this disclosure.
Figure 1B:
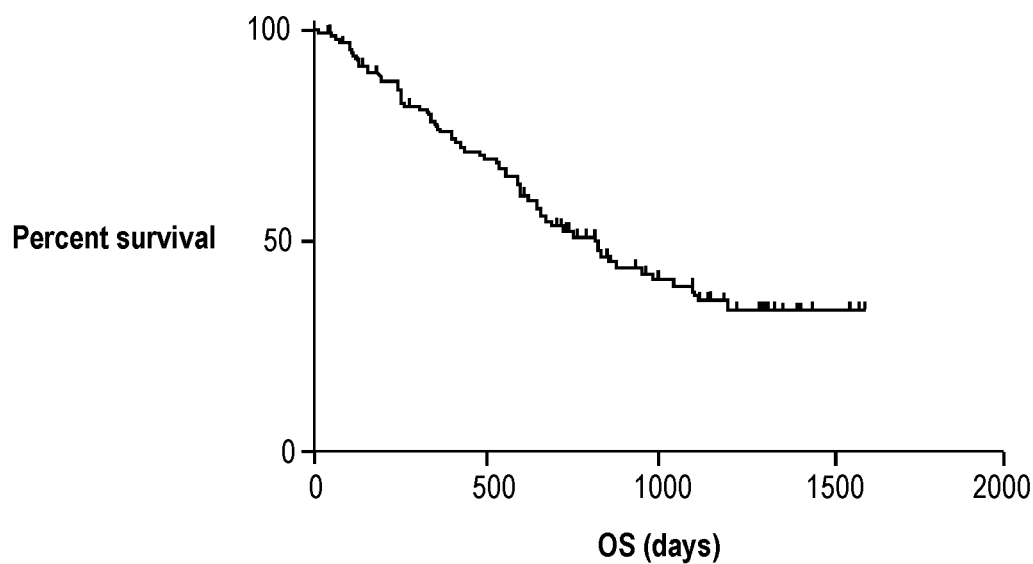

Kaplan-Meier plots for progression-free survival (PFS) and overall survival (OS) for the cohort of 114 patients with baseline samples and acquired spectra are shown in FIGS. 1A and 1B, respectively. Response data is summarized in table 1. Median OS is 813 days (95% CI: 623-1037 days) and median PFS is 79 days (95% CI: 69-94 days).

TABLE 1

Response data for all 114 patients with available clinical data and spectra from pretreatment samples

|   | n (%) |
|---|---|
| CR | 8 (7) |
| PR | 13 (11) |
| Minimal Response | 6 (5) |
| SD | 26 (23) |
| PD | 60 (53) |
| NE/NA | 1 (1) |

All patients with complete response are still progression-free, with median follow up time of 1092 days (range 184-1547 days). Four of the 13 partial responders are still progression-free, with median follow up time of 1026 days (range 697-1435).

Sample Preparation

Samples were thawed and 3 µl aliquots of each experimental sample (i.e. one of the samples from patients subsequently treated with IL2) and quality control serum (a pooled sample obtained from serum of five healthy patients, purchased from ProMedDx, "SerumP3") spotted onto VeriStrat® serum cards (Therapak). The cards were allowed to dry for 1 hour at ambient temperature after which the whole serum spot was punched out with a 6 mm skin biopsy punch (Acuderm). Each punch was placed in a centrifugal filter with 0.45 µm nylon membrane (VWR). One hundred µl of HPLC grade water (JT Baker) was added to the centrifugal filter containing the punch. The punches were vortexed gently for 10 minutes then spun down at 14,000 rcf for two minutes. The flow-through was removed and transferred back on to the punch for a second round of extraction. For the second round of extraction, the punches were vortexed gently for three minutes then spun down at 14,000 rcf for two minutes. Twenty microliters of the filtrate from each sample was then transferred to a 0.5 ml eppendorf tube for MALDI analysis.

All subsequent sample preparation steps were carried out in a custom designed humidity and temperature control chamber (Coy Laboratory). The temperature was set to 30° C. and the relative humidity at 10%.

An equal volume of freshly prepared matrix (25 mg of sinapinic acid per 1 ml of 50% acetonitrile: 50% water plus 0.1% TFA) was added to each 20 µl serum extract and the mix vortexed for 30 sec. The first three aliquots (3×2 µl) of sample:matrix mix were discarded into the tube cap. Eight aliquots of 2 µl sample:matrix mix were then spotted onto a stainless steel MALDI target plate (SimulTOF). The MALDI target was allowed to dry in the chamber before placement in the MALDI mass spectrometer.

This set of samples was processed for MALDI analysis in four batches. QC samples were added to the beginning (two preparations) and end (two preparations) of each batch run.

Spectral Acquisition

MALDI spectra were obtained using a MALDI-TOF mass spectrometer (SimulTOF 100 s/n: LinearBipolar 11.1024.01 from Virgin Instruments, Marlborough, Mass., USA). The instrument was set to operate in positive ion mode, with ions generated using a 349 nm, diode-pumped, frequency-tripled Nd:YLF laser operated at a laser repetition rate of 0.5 kHz. External calibration was performed using the following peaks in the QC serum spectra: m/z=3320 Da, 4158.7338 Da, 6636.7971 Da, 9429.302 Da, 13890.4398 Da, 15877.5801 Da and 28093.951 Da.

Spectra from each MALDI spot were collected as 800 shot spectra that were 'hardware averaged' as the laser fires continuously across the spot while the stage is moving at a speed of 0.25 mm/sec. A minimum intensity threshold of 0.01 V was used to discard any 'flat line' spectra. All 800 shot spectra with intensity above this threshold were acquired without any further processing.

Spectral Processing

Raster Spectra Preprocessing

Alignment and Filtering

Each raster spectrum of 800 shots was processed through an alignment workflow to align prominent peaks to a set of 43 alignment points (see table 2). A filter was applied that essentially smooths noise and spectra were background subtracted for peak identification. Given the identified peaks, the filtered spectra (without background subtraction) were aligned. Additional filtering parameters required that raster spectra have at least 20 peaks and used at least 5 alignments to be included in the pool of rasters used to assemble the average spectrum.

TABLE 2

Alignment points used to align the raster spectra

| M/z |
|---|
| 3168.00 |
| 4153.48 |
| 4183.00 |
| 4792.00 |
| 5773.00 |
| 5802.00 |
| 6432.79 |
| 6631.06 |
| 7202.00 |
| 7563.00 |
| 7614.00 |
| 7934.00 |
| 8034.00 |
| 8206.35 |
| 8684.25 |
| 8812.00 |
| 8919.00 |
| 8994.00 |

TABLE 2-continued

Alignment points used
to align the raster spectra
M/z 9133.25
9310.00
9427.00
10739.00
10938.00
11527.06
12173.00
12572.38
12864.24
13555.00
13762.87
13881.55
14039.60
14405.00
15127.49
15263.00
15869.06
17253.06
18629.76
21065.65
23024.00
28090.00
28298.00

Raster Averaging

Averages were created from the pool of aligned and filtered raster spectra. A random selection of 500 raster spectra was averaged to create a final analysis spectrum for each sample of 400,000 laser shots.

Deep MALDI Average Spectra Preprocessing

Background Estimation and Subtraction

The two window method of background estimation and subtraction was used as it was discovered that this method better estimates the background in regions where small peaks are surrounded by much larger peaks. Table 3 lists the windows that were used for estimation and subtraction of background from the analysis spectra (averages).

TABLE 3

Background estimation windows

|  | m/z | width |
|---|---|---|
| Wide windows | | |
| | 3000 | 60000 |
| | 30000 | 60000 |
| | 31000 | 100000 |
| Medium windows | | |
| | 3000 | 7500 |
| | 30000 | 7500 |
| | 31000 | 10000 |

Normalization by Bin Method

The bin method was used to compare clinical groups of interest to ensure that normalization windows are not selected that have desirable characteristics for distinguishing the groups of interest. The normalization windows were reduced using the reference replicates spotted alongside the IL2 samples on each plate to remove features that are intrinsically unstable. To do this, a CV cutoff of 0.2 was applied. Normalization windows with CVs greater than 0.2 were rejected from consideration. To further prune the normalization windows, disease control status (DCR) was used to compare features. A p value cutoff of 0.5 was applied (features below 0.5 were rejected) and a CV cutoff of 0.65 (features above 0.65 were rejected). As a final step, clinical groups defined as Early (with OS below the median OS) and Late (with OS above the median OS) were compared. Features with P values below 0.5 and CVs greater than 0.80 were removed. The remaining features used as normalization windows are listed below in table 4.

TABLE 4

Normalization
by bin windows

| Left M/z | Right M/z |
|---|---|
| 3785.03 | 4078.74 |
| 4324.18 | 4390.64 |
| 4491.64 | 4688.07 |
| 4689.55 | 4742.28 |
| 4744.51 | 4799.83 |
| 4801.32 | 4874.47 |
| 4946.13 | 5077.58 |
| 5080.92 | 5259.89 |
| 6377.92 | 6510.48 |
| 7229.72 | 7513.77 |
| 8402.18 | 8498.62 |
| 9054.25 | 9171.92 |
| 9172.81 | 9271.02 |
| 9547.95 | 9811.60 |
| 10908.61 | 11356.51 |
| 19212.92 | 20743.82 |

Figure 2:
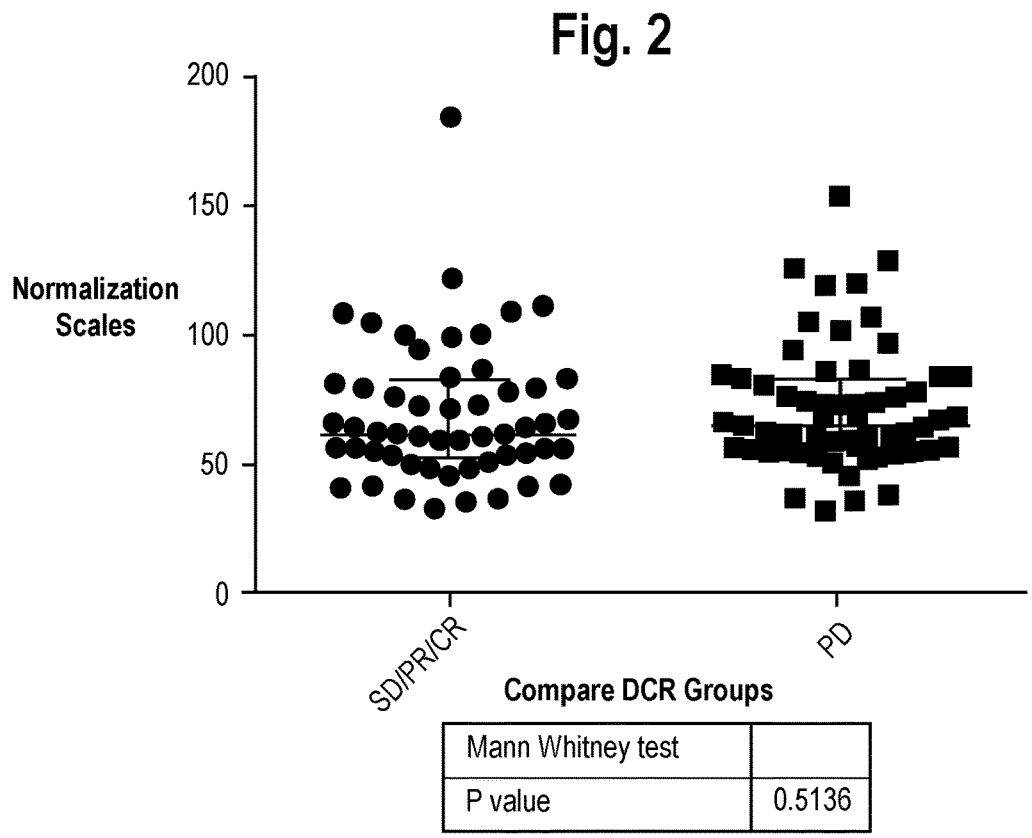
FIG. 2 is a plot of the distribution of normalization scalars by disease control rate (DCR) groups.
Figure 3:
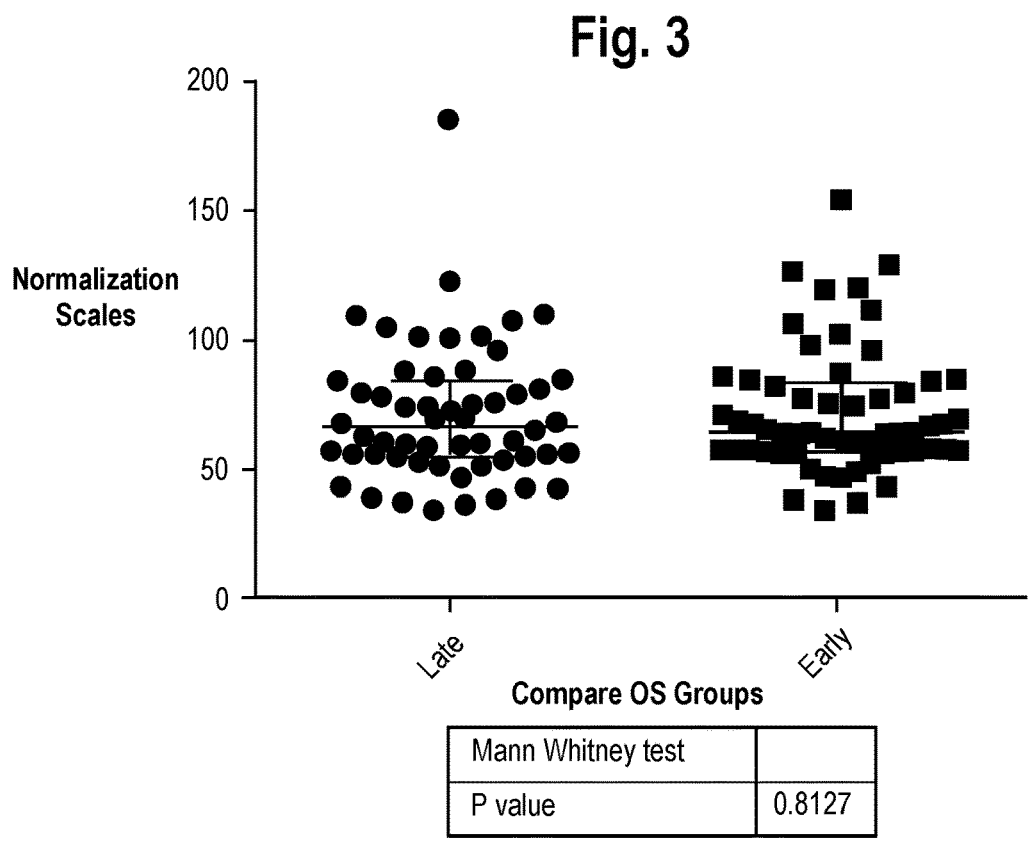
FIG. 3 is a plot of the distribution of normalization scalars by overall survival groups.

The resulting normalization scalars were compared between the groups to ensure the combination of windows was not significantly associated with groups. The plots of FIGS. 2 and 3 demonstrate that the distribution of normalization scalars is not associated with the clinical groups of interest.

Average Spectra Alignment

The peak alignment of the average spectra is typically very good; however, a fine-tune alignment step was performed to address minor differences in peak positions in the spectra. A set of alignment points was identified and applied to the analysis spectra (table 5).

TABLE 5

Calibration points used
to align the spectral averages
M/z 3315.17
4153.33
4456.88
4709.91
5066.47
6432.85
6631.27
7934.36
8916.29
9423.10
9714.25
12868.19
13766.39
14044.69
14093.30
15131.43
15871.93
16077.64
17255.58
17383.45
18630.93
21069.05
21168.45
28084.44
28292.86
67150.37

Feature Definitions

Figure 4:
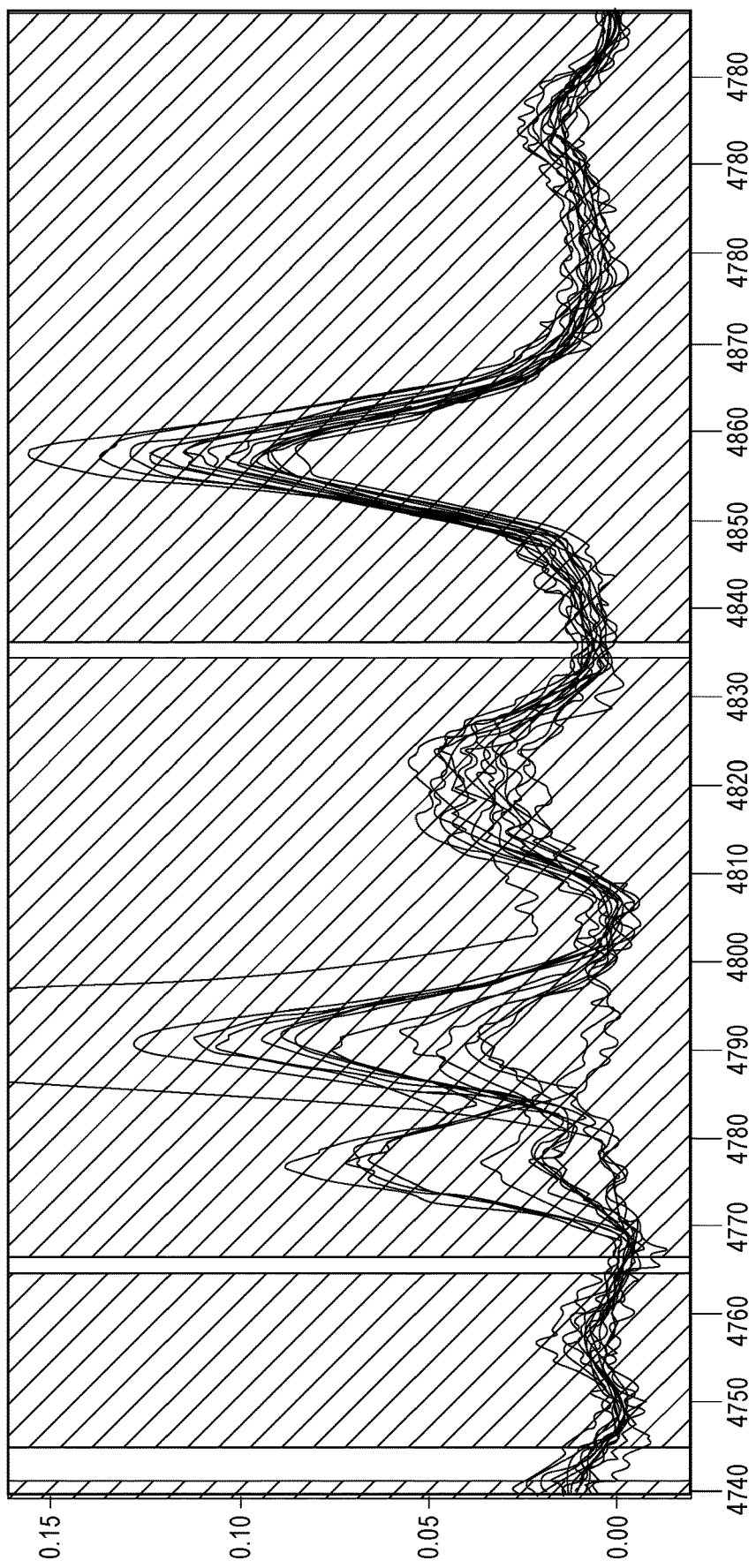
FIG. 4 is portion of a mass spectrum showing definitions of features (peaks).

Feature definitions (peaks in the spectra) were selected in an iterative process over the batches. Several spectra were loaded simultaneously and features defined. The entire M/z region of interest was examined and all features were defined. After the first round, a second set of spectra were examined. Some features were not optimally defined from the first round and were adjusted to meet requirements of the second set of spectra. New features were identified that were not present in the first set of spectra. This process was continued until the final set was determined. As a final step, each batch was examined to determine if any additional features could be defined that could only be identified with knowledge from many spectra loaded simultaneously. Several features were identified that may have heightened susceptibility to peptide modifications that take place during the sample preparation procedure. These manifest in spectra as specific m/z regions where the peaks change in intensity and shape dependent on the position on the plate where the sample was spotted. These regions were excluded from feature selection. A final set of 326 feature definitions was applied to the spectra and is listed in Table 32. An example of features defined using the described method is displayed in FIG. 4 with the SP3 reference spectra and spectra from batch 1 indicated.

Batch Correction of Analysis Spectra
SerumP3 analysis

Two preparations of the reference sample, SerumP3, were plated at the beginning (1,2) and end (3,4) of each run. The purpose of these samples is to ensure that variations by batch due to slight changes in instrument performance (for example, aging of the detector) can be corrected for.

To perform batch correction, one spectrum, which is an average of one of the preparations from the beginning and one from the end of the batch, must serve as the reference for the batch. The procedure used for selecting the pair is described first.

The reference samples were preprocessed as described above. All 326 features were used to evaluate the possible combinations (1-3, 1-4, 2-3, 2-4). We compared each possible combination of replicates using the function:

$$A = \min(\text{abs}(1-\text{ftrval1}/\text{ftrval2}), \text{abs}(1-\text{ftrval2}/\text{ftrval1}))$$

where ftrval1 (ftrval2) is the value of a feature for the first (second) replicate of the replicate pair. This quantity A gives a measure of how similar the replicates of the pair are. For each feature, A is reported. If the value is >0.5, then the feature is determined to be discordant, or 'Bad'. A tally of the bad features is reported for each possible combination. If the value of A is <0.1, then the feature is determined to be concordant and reported as 'Good'. A tally of the Good features is reported for each possible combination. Using the tallies of Bad and Good features from each possible combination, we computed the ratio of Bad/Good. The combination with the lowest ratio was reported as the most similar combination, unlikely to contain any systematic or localized outlier behavior in either of the reference spectra. If no ratio can be found that is less than 0.12, then the batch is declared a failure. Table 6 reports the combinations that were found most similar for each batch.

TABLE 6

SerumP3 preparations found to be most similar by batch

| Batch | Combination |
| --- | --- |
| IL1_B1 | 2_3 |
| IL2_B2 | 2_4 |
| IL2_B3 | 1_4 |
| IL2_B4 | 2_3 |

Batch Correction

Batch 1 was used as the baseline batch to correct all other batches. The reference sample was used to find the correction coefficients for each of the batches 2-4 by the following procedure.

Within each batch j ($2 \leq j \leq 4$), the ratio $$\hat{r}_i^j = \frac{A_i^j}{A_i^1}$$

and the average amplitude $\overline{A}_i^j = \frac{1}{2}(A_i^j + A_i^1)$ are defined for each $i^{th}$ feature centered at $(m/z)_i$, where $A_i^j$ is the average reference spectra amplitude of feature i in the batch being corrected and $A_i^1$ is the reference spectra amplitude of feature i in batch 1 (the reference standard). It is assumed that the ratio of amplitudes between two batches follows the dependence $$r(\overline{A},(m/z)) = (a_0 + a_1 \ln(\overline{A})) + (b_0 + \overline{A})(m/z) + c_0(m/z)^2.$$

On a batch to batch basis, a continuous fit is constructed by minimizing the sum of the square residuals, $\Delta^j = \Sigma_i (\hat{r}_i^j - r^j (a_0, a_1, b_0, b_1, c_0))^2$, and using the experimental data of the reference sample. The SerumP3 reference samples are used to calculate the correction function. Steps were taken to not include outlier points in order to avoid bias in the parameter estimates. The values of the coefficients $a_0, a_1, b_0, b_1$ and $c_0$, obtained for the different batches are listed in Appendix B (table B.1) of prior provisional application Ser. No. 62/369,289 filed Aug. 1, 2016. The projection in the $\hat{r}_i^j$ versus $(m/z)_i$ plane of the points used to construct the fit for each batch of reference spectra, together with the surface defined by the fit itself, can be plotted but the details are not particularly important and omitted for the sake of brevity.

Once the final fit, $r^j(\overline{A},(m/z))$, is determined for each batch, the next step is to correct, for all the samples, all the features (with amplitude A at (m/z)) according to $$A_{corr} = \frac{A}{r^j(\overline{A}, (m/z))}.$$

After this correction, the corrected, $(\overline{A}_i^j,(m/z)_i,\hat{r}_i^j)$ feature values calculated for reference spectra lie around the horizontal line defined by =1. Post correction coefficients are calculated to compare to quality control thresholds. These coefficients can be found in Appendix B table B.2 of prior provisional application Ser. No. 62/369,289 filed Aug. 1, 2016.

Partial Ion Current (PIC) Normalization

The dataset was combined (batches 1-4) and examined to find regions of intrinsic stability to use as the final normalization windows. First, the univariate p values were found by comparing the DCR groups across all features. Features with p values less than 0.15 were excluded from the PIC analysis as these features may contribute meaningful information in test development. In a second screen, p values comparing OS groups (Early and Late) were computed. Again features with p values less than 0.15 were excluded from the PIC analysis. A set of 222 features were used in the PIC analysis, of which 21 were used for the final PIC normalization (Table 7). Further details on partial ion current normalization of mass spectra is found in U.S. Pat. No. 7,736,905, the content of which is incorporated by reference herein.

TABLE 7

Features used for PIC normalization
M/z

| M/z |
|---|
| 3681 |
| 3776 |
| 3952 |
| 4010 |
| 4590 |
| 6081 |
| 6194 |
| 6921 |
| 6947 |
| 6971 |
| 7021 |
| 7035 |
| 7053 |
| 13845 |
| 14051 |
| 14100 |
| 21066 |
| 21173 |
| 21272 |
| 21373 |

Figure 5:
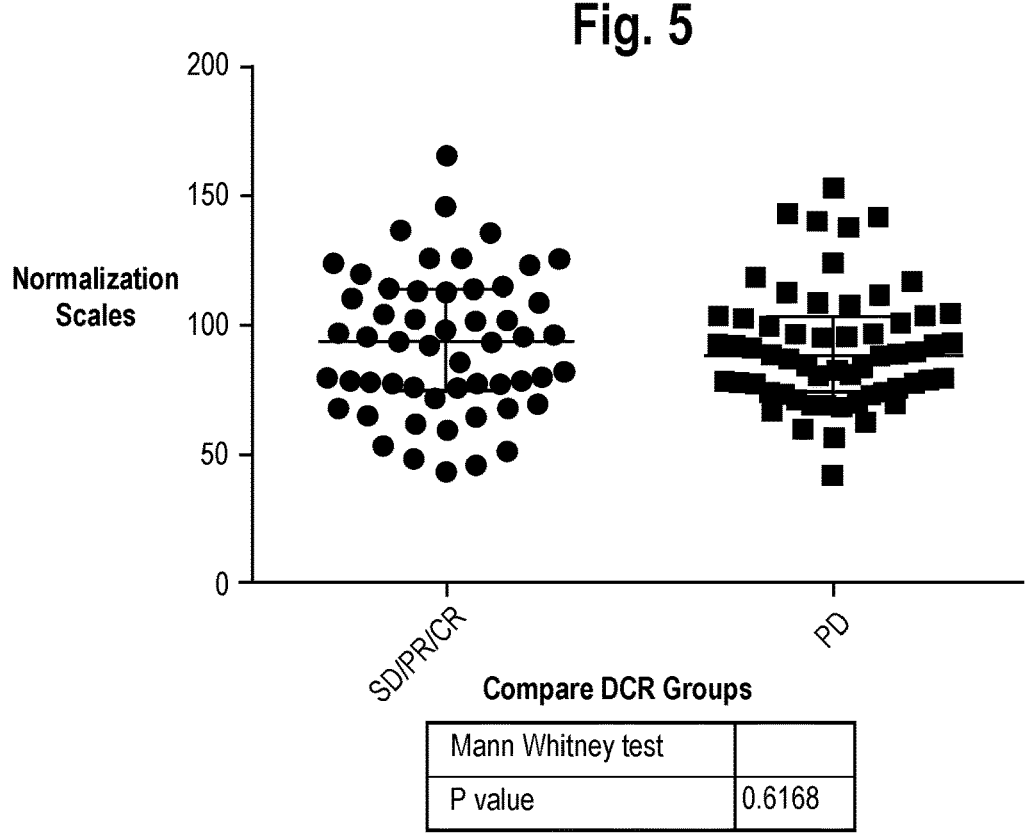
FIG. 5 is a plot of partial ion current normalization scalars by DCR groups.
Figure 6:
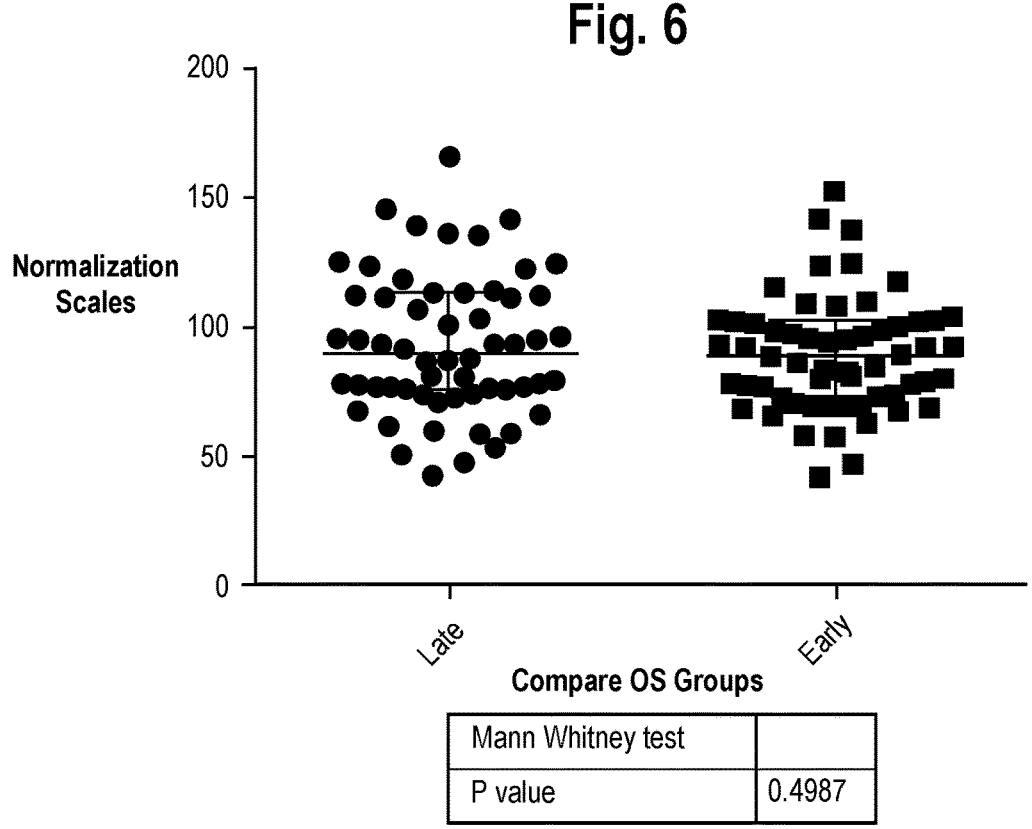
FIG. 6 is a plot of partial ion current normalization scalars by overall survival groups.

To normalize, the feature values from the listed features were summed for each spectrum to compute a normalization scalar. All feature values were then divided by the normalization scalar to arrive at the final table used in the diagnostic cortex. The normalization scalars were again examined by clinical group to test that the combined features, i.e. the scalars themselves, were not correlated with group. The plots of FIGS. 5 and 6 illustrate the distribution of the scalars by group. The plots for the two groups are very similar, indicating that the normalization scalars are appropriate to use.

Once the final features have been defined and the spectra subject to the above preprocessing routines (including background subtraction), feature values are obtained for each of the features listed in Table 32 for each of the samples in the development set. This is the "feature table" in the following discussion.

B. Classifier Development (FIG. 7)

Figure 7A:
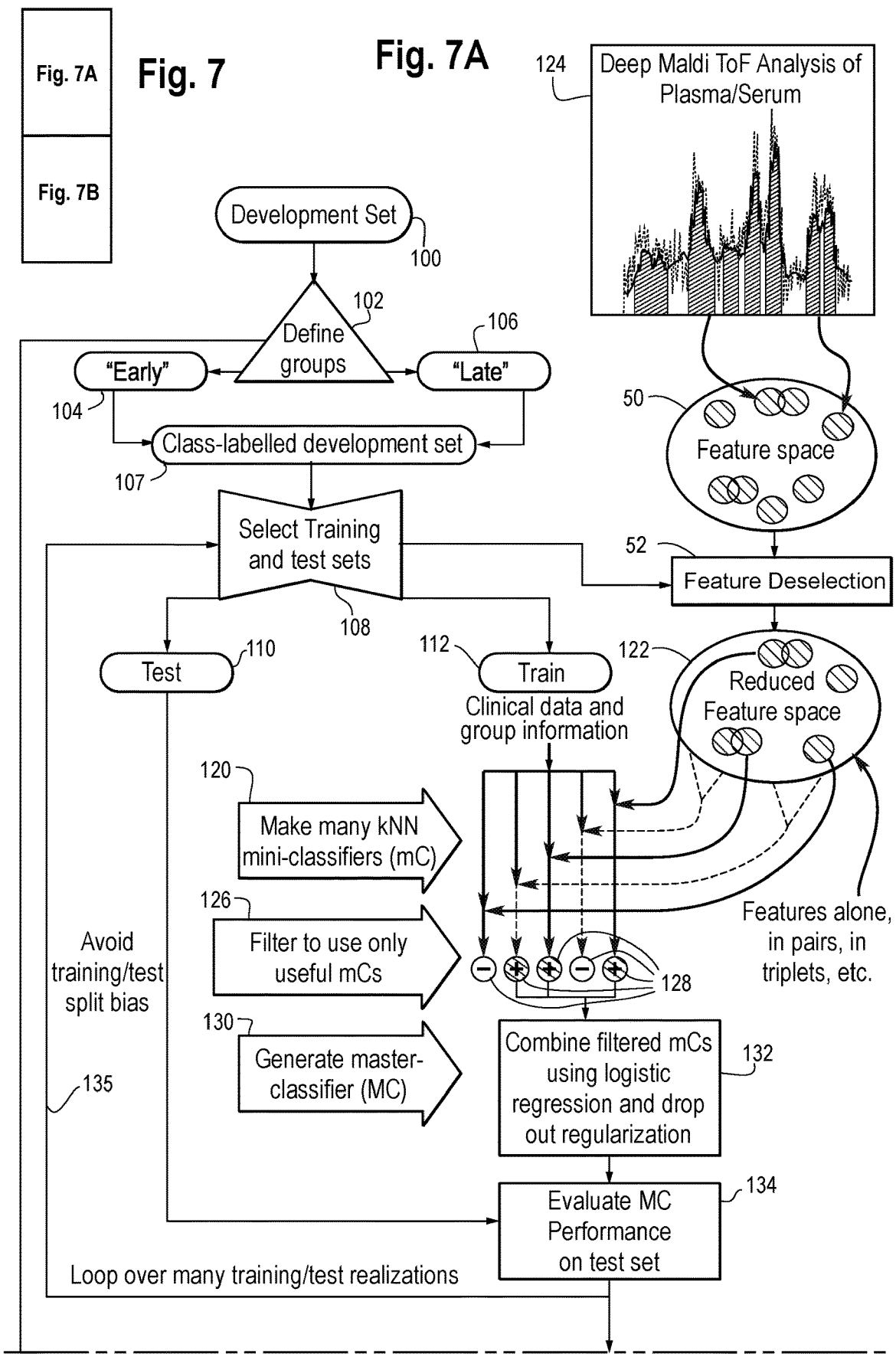
FIGS. 7A and 7B are a flow chart of a computer-implemented procedure for classifier generation which is referred to as "Diagnostic Cortex." The methodology of FIG. 7A-7B was applied to the mass spectral data from the development sample set and resulted in a classifier (i.e., a set of parameters stored in the computer) which makes predictions of melanoma patient benefit from high dose IL2 therapy in advance of treatment.
Figure 7B:
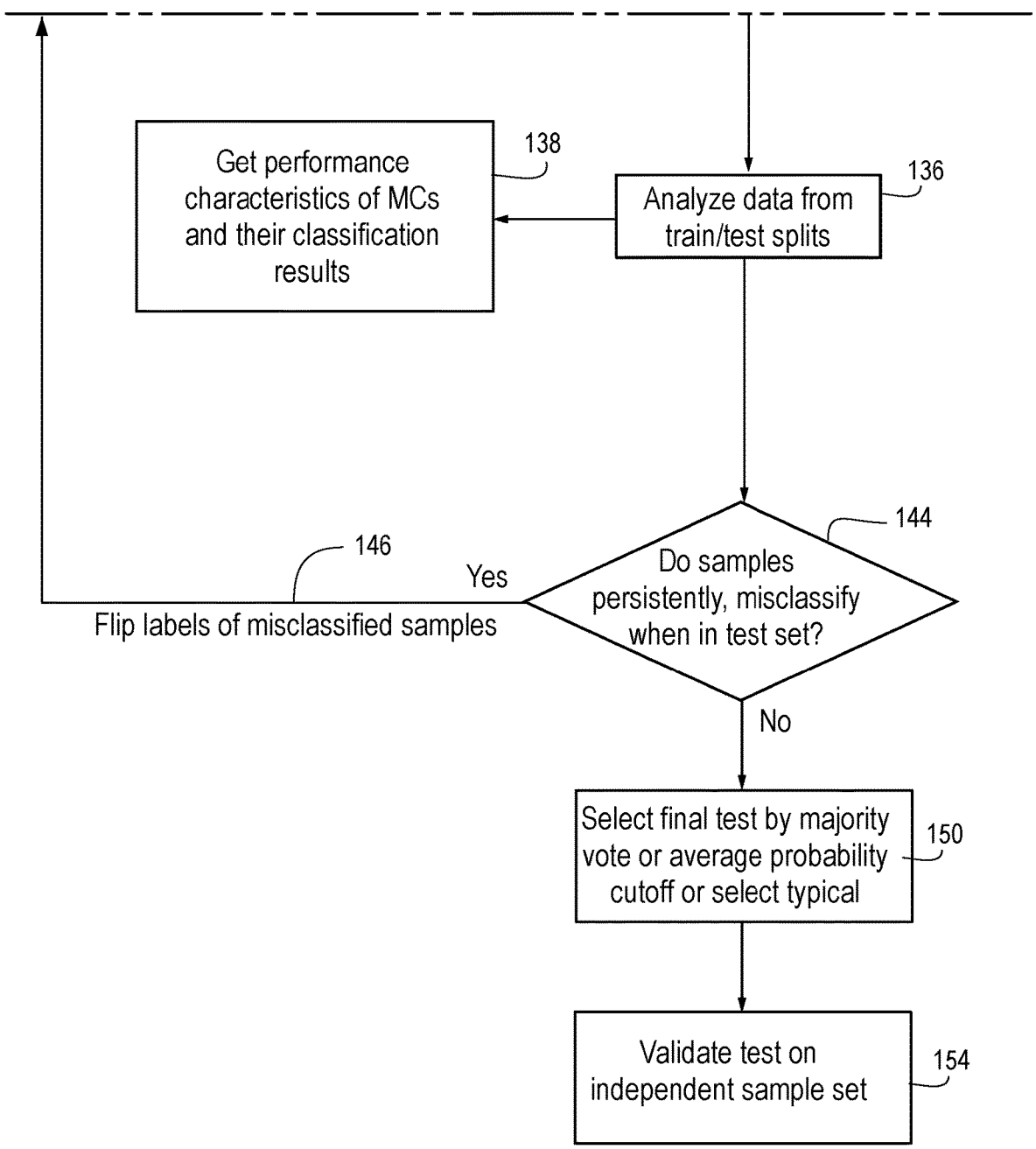

After the feature table for features in the mass spectra for the 114 samples was created (as explained above) we proceeded to develop with the aid of a programmed computer a classifier using the classifier generation method shown in flow-chart form in FIGS. 7A-7B. This method, known as "combination of mini-classifiers with drop-out regularization" or "CMC/D", or DIAGNOSTIC CORTEX™, is described at length in U.S. Pat. No. 9,477,906 of H. Röder et al., the entire content of which is incorporated by reference herein. An overview and rationale of the methodology will be provided here first, and then illustrated in detail in conjunction with FIG. 7 for the generation of the melanoma/IL2 classifier.

In contrast to standard applications of machine learning focusing on developing classifiers when large training data sets are available, the big data challenge, in bio-life-sciences the problem setting is different. Here we have the problem that the number (n) of available samples, arising typically from clinical studies, is often limited, and the number of attributes (measurements) (p) per sample usually exceeds the number of samples. Rather than obtaining information from many instances, in these deep data problems one attempts to gain information from a deep description of individual instances. The present methods take advantage of this insight, and are particularly useful, as here, in problems where $p \gg n$.

The method includes a first step a) of obtaining measurement data for classification from a multitude of samples, i.e., measurement data reflecting some physical property or characteristic of the samples. The data for each of the samples consists of a multitude of feature values, and a class label. In this example, the data takes the form of mass spectrometry data, in the form of feature values (integrated peak intensity values at a multitude of M/z ranges or peaks, see Table 32) as well as a label indicating some attribute of the sample (for example, patient Early or Late death or disease progression). In this example, the class labels were assigned by a human operator to each of the samples after investigation of the clinical data associated with the sample. The development sample set is then split into a training set and a test set and the training set is used in the following steps b), c) and d).

The method continues with a step b) of constructing a multitude of individual mini-classifiers using sets of feature values from the samples up to a pre-selected feature set size s (s=integer 1 . . . n). For example a multiple of individual mini- or atomic classifiers could be constructed using a single feature (s=1), or pairs of features (s=2), or three of the features (s=3), or even higher order combinations containing more than 3 features. The selection of a value of s will normally be small enough to allow the code implementing the method to run in a reasonable amount of time, but could be larger in some circumstances or where longer code run-times are acceptable. The selection of a value of s also may be dictated by the number of measurement data values (p) in the data set, and where p is in the hundreds, thousands or even tens of thousands, s will typically be 1, or 2 or possibly 3, depending on the computing resources available. The mini-classifiers execute a supervised learning classification algorithm, such as k-nearest neighbors (kNN), in which the values for a features, pairs or triplets of features of a sample instance are compared to the values of the same feature or features in a training set and the nearest neighbors (e.g., k=9) in an s-dimensional feature space are identified and by majority vote a class label is assigned to the sample instance for each mini-classifier. In practice, there may be thousands of such mini-classifiers depending on the number of features which are used for classification.

The method continues with a filtering step c), namely testing the performance, for example the accuracy, of each of the individual mini-classifiers to correctly classify the sample, or measuring the individual mini-classifier performance by some other metric (e.g. the difference between the Hazard Ratios (HRs) obtained between groups defined by the classifications of the individual mini-classifier for the training set samples) and retaining only those mini-classifiers whose classification accuracy, predictive power, or other performance metric, exceeds a pre-defined threshold is within pre-set limits to arrive at a filtered (pruned) set of mini-classifiers. The class label resulting from the classification operation may be compared with the class label for the sample known in advance if the chosen performance metric for mini-classifier filtering is classification accuracy. However, other performance metrics may be used and evaluated using the class labels resulting from the classification operation. Only those mini-classifiers that perform reasonably well under the chosen performance metric for classification are maintained. Alternative supervised classification algorithms could be used, such as linear discriminants, decision trees, probabilistic classification methods, margin-based classifiers like support vector machines, and any other classification method that trains a classifier from a set of labeled training data.

To overcome the problem of being biased by some univariate feature selection method depending on subset bias, we take a large proportion of all possible features as candidates for mini-classifiers. We then construct all possible kNN classifiers using feature sets up to a pre-selected size (parameter s). This gives us many "mini-classifiers": e.g. if we start with 100 features for each sample (p=100), we would get 4950 "mini-classifiers" from all different possible combinations of pairs of these features (s=2), 161,700 mini-classifiers using all possible combination of three features (s=3), and so forth. Other methods of exploring the space of possible mini-classifiers and features defining them are of course possible and could be used in place of this hierarchical approach. Of course, many of these "mini-classifiers" will have poor performance, and hence in the filtering step c) we only use those "mini-classifiers" that pass predefined criteria. These filtering criteria are chosen dependent on the particular problem: If one has a two-class classification problem, one would select only those mini-classifiers whose classification accuracy exceeds a predefined threshold, i.e., are predictive to some reasonable degree. Even with this filtering of "mini-classifiers" we end up with many thousands of "mini-classifier" candidates with performance spanning the whole range from borderline to decent to excellent performance.

The method continues with step d) of generating a master classifier (MC) by combining the filtered mini-classifiers using a regularized combination method. In one embodiment, this regularized combination method takes the form of repeatedly conducting a logistic training of the filtered set of mini-classifiers to the class labels for the samples. This is done by randomly selecting a small fraction of the filtered mini-classifiers as a result of carrying out an extreme dropout from the filtered set of mini-classifiers (a technique referred to as drop-out regularization herein), and conducting logistical training on such selected mini-classifiers. While similar in spirit to standard classifier combination methods (see e.g. S. Tulyakov et al., Review of Classifier Combination Methods, Studies in Computational Intelligence, Volume 90, 2008, pp. 361-386), we have the particular problem that some "mini-classifiers" could be artificially perfect just by random chance, and hence would dominate the combinations. To avoid this overfitting to particular dominating "mini-classifiers", we generate many logistic training steps by randomly selecting only a small fraction of the "mini-classifiers" for each of these logistic training steps. This is a regularization of the problem in the spirit of dropout as used in deep learning theory. In this case, where we have many mini-classifiers and a small training set we use extreme dropout, where in excess of 99% of filtered mini-classifiers are dropped out in each iteration.

In more detail, the result of each mini-classifier is one of two values, either "Early" or "Late" in this example. We can then combine the results of the mini-classifiers in the spirit of a logistic regression by defining the probability of obtaining an "Early" label via standard logistic regression (see e.g. http://en.wikipedia.org/wiki/Logistic_regression)

$$P(\text{"Early"} | \text{feature for a spectrum}) = \frac{\exp\left(\sum_{\text{mini classifiers}} w_{mc} I(mc(\text{feature values}))\right)}{\text{Normalization}} \quad \text{Eq. (1)}$$

where $I(mc(\text{feature values}))=1$, if the mini-classifier mc applied to the feature values of a sample returns "Early", and 0 if the mini-classifier returns "Late". The weights $w_{mc}$ for the mini-classifiers are unknown and need to be determined from a regression fit of the above formula for all samples in the training set using +1 for the left hand side of the formula for the Late-labeled samples in the training set, and 0 for the Early-labeled samples, respectively. As we have many more mini-classifiers, and therefore weights, than samples, typically thousands of mini-classifiers and only tens of samples, such a fit will always lead to nearly perfect classification, and can easily be dominated by a mini-classifier that, possibly by random chance, fits the particular problem very well. We do not want our final test to be dominated by a single special mini-classifier which only performs well on this particular set and is unable to generalize well. Hence we designed a method to regularize such behavior: Instead of one overall regression to fit all the weights for all mini-classifiers to the training data at the same time, we use only a few of the mini-classifiers for a regression, but repeat this process many times in generating the master classifier. For example we randomly pick three of the mini-classifiers, perform a regression for their three weights, pick another set of three mini-classifiers, and determine their weights, and repeat this process many times, generating many random picks, i.e. realizations of three mini-classifiers. The final weights defining the master classifier are then the averages of the weights over all such realizations. The number of realizations should be large enough that each mini-classifier is very likely to be picked at least once during the entire process. This approach is similar in spirit to "drop-out" regularization, a method used in the deep learning community to add noise to neural network training to avoid being trapped in local minima of the objective function.

Other methods for performing the regularized combination method in step (d) that could be used include:

Logistic regression with a penalty function like ridge regression (based on Tikhonov regularization, Tikhonov, Andrey Nikolayevich (1943). "Об устойчивости обратных задач" [On the stability of inverse problems]. Doklady Akademii Nauk SSSR 39 (5): 195-198.)

The Lasso method (Tibshirani, R. (1996). Regression shrinkage and selection via the lasso. J. Royal. Statist. Soc B., Vol. 58, No. 1, pages 267-288).

Neural networks regularized by drop-out (Nitish Shrivastava, "Improving Neural Networks with Dropout", Master's Thesis, Graduate Department of Computer Science, University of Toronto), available from the website of the University of Toronto Computer Science department.

General regularized neural networks (Girosi F. et al, Neural Computation, (7), 219 (1995)).

The above-cited publications are incorporated by reference herein. Our approach of using drop-out regularization has shown promise in avoiding over-fitting, and increasing the likelihood of generating generalizable tests, i.e. tests that can be validated in independent sample sets.

"Regularization" is a term known in the art of machine learning and statistics which generally refers to the addition of supplementary information or constraints to an underdetermined system to allow selection of one of the multiplicity of possible solutions of the underdetermined system as the unique solution of extended system. Depending on the nature of the additional information or constraint applied to "regularize" the problem (i.e. specify which one or subset of the many possible solutions of the unregularized problem should be taken), such methods can be used to select solutions with particular desired properties (e.g. those using fewest input parameters or features) or, in the present context of classifier training from a development sample set, to help avoid overfitting and associated lack of generalization (i.e., selection of a particular solution to a problem that performs very well on training data but only performs very poorly or not all on other datasets). See e.g., https://en.wikipedia.org/wiki/Regularization_(mathematics). One example is repeatedly conducting extreme dropout of the filtered mini-classifiers with logistic regression training to classification group labels. However, as noted above, other regularization methods are considered equivalent. Indeed it has been shown analytically that dropout regularization of logistic regression training can be cast, at least approximately, as L2 (Tikhonov) regularization with a complex, sample set dependent regularization strength parameter λ (S Wager, S Wang, and P Liang, Dropout Training as Adaptive Regularization, Advances in Neural Information Processing Systems 25, pages 351-359, 2013 and D Helmbold and P Long, On the Inductive Bias of Dropout, JMLR, 16:3403-3454, 2015) In the term "regularized combination method" the "combination" simply refers to the fact that the regularization is performed over combinations of the mini-classifiers which pass filtering. Hence, the term "regularized combination method" is used to mean a regularization technique applied to combinations of the filtered set of mini-classifiers so as to avoid overfitting and domination by a particular mini-classifier.

The performance of the master classifier is then evaluated by how well it classifies the subset of samples forming the test set.

In step e), steps b)-d) are repeated in the programmed computer for different realizations of the separation of the set of samples into test and training sets, thereby generating a plurality of master classifiers, one for each realization of the separation of the set of samples into training and test sets. The performance of the classifier is evaluated for all the realizations of the separation of the development set of samples into training and test sets. If there are some samples which persistently misclassify when in the test set, the process optionally loops back and steps b), c) and d) and e) are repeated with flipped class labels for such misclassified samples.

The method continues with step f) of defining a final classifier from one or a combination of more than one of the plurality of master classifiers. In the present example, the final classifier is defined as a majority vote of all the master classifiers resulting from each separation of the sample set into training and test sets, or alternatively by an average probability cutoff.

Turning now to FIG. 7A-7B, the classifier development process will be described in further detail in the context of the melanoma/IL2 classifier. In FIG. 7A, the "development set" 100 is the set of 114 samples we used for classifier development and the associated mass spectrometry data. The samples were subject to deep MALDI and integrated intensity values of selected features (see 124) were calculated and stored as a feature table (see feature space 50).

Definition of Class Labels (102)

In our procedure of FIG. 7 we need to assign a class label to each of the samples in step 102. Time-to-event data was used for classifier training. In this situation class labels are not obvious and, as shown in FIG. 7A, the diagnostic cortex uses an iterative method to refine class labels at the same time as creating/training the classifier. An initial guess is made for the class labels. Typically the samples are sorted on either PFS or OS and half of the samples with the lowest time-to-event outcome are assigned the "Early" class label (early death or progression, i.e. poor outcome) while the other half are assigned the "Late" class label (late death or progression, i.e. good outcome). For the classifiers discussed in this report both OS and PFS was used. A classifier is then constructed using the outcome data and these class labels. This classifier can then be used to generate classifications for the development set samples and these are then used as the new class labels for a second iteration of the classifier construction step. This process is iterated until convergence. The group of samples with the class label Early is shown at 104 and the group of samples with the Late class label is shown at 106. We therefore have a class labeled development set as shown at 107.

At step 108, we split the class labeled development set into training and test sets, in a random manner assigning one half of the samples into a training set 112 and another half in a test set 110. In practice, many (e.g., hundreds) of separations of the development set into training and test sets are identified so that the process can loop as indicated at loop 135 over each one of these different realizations.

Feature Deselection or Feature Selection (step 52)

To be able to consider all subsets of three or more features or to attempt to improve classifier performance by dropping noisy features (those not useful for classification) it may be necessary or desirable to deselect features that are not useful for classification from the set of 326 features. This is done at step 52. Removal or deselection of features likely to be of negligible use for classification is done using a bagged feature deselection approach in which the ability of individual features to classify samples (using kNN classification) is tested across multiple randomly-drawn subsets of the development set and features deselected that display no consistent univariate classification potential across the many subsets. This results in a reduced feature space 122. Further details on feature deselection are set forth in Appendix C of our prior provisional application Ser. No. 62/369,289 filed Aug. 1, 2016; see also pending U.S. patent application of J. Roder et al., Ser. No. 15/091,417 filed Apr. 5, 2016 published as US patent application publication 2016/0321561, and in U.S. provisional application Ser. No. 62/319,958 filed Apr. 8, 2016, the content of which is incorporated by reference herein. Feature selection based on the development sample set is prone to overfitting and always avoided. However, in one embodiment we do use a method where subsets of features are selected from the set of 326 available features based on their association with particular biological functions as determined by a gene set enrichment analysis (GSEA) on a separate sample set. This is explained in more detail in Appendix D of our prior provisional application Ser. No. 62/369,289 filed Aug. 1, 2016. The methodology of GSEA to identify mass spectral features with particular biological functions is also set forth in U.S. patent application Ser. No. 15/207,825 filed Jul. 12, 2016 and in the articles V K Mootha, C M Lindgren, K-F Eriksson, et al., *PGC-1α-responsive genes involved in oxidative phosphorylation are coordinately downregulated in human diabetes*. Nat Genet. 2003; 34(3):267-73 and A Subramanian, P Tamayo, V K Mootha, et al., *Gene set enrichment analysis: A knowledge-based approach for interpreting genome-wide expression profiles*. Proc Natl Acad Sci USA 2005; 102(43): 15545-50. A further description is therefore omitted for the sake of brevity.

Table 33 lists reduced sets of features which were used for classifier training for Classifier 1 and Classifier 2 in the following discussion.

Creation and Filtering of Mini-Classifiers (Steps 120 and 126)

The development set samples 107 are split into training and test sets (110, 112) in multiple different random realizations, i.e., iterations through the loop 135. Six hundred and twenty five realizations were used for this project. The procedure of FIG. 7A-7B works best when training classes (Early and Late) have the same number of samples. Hence, if classes have different numbers of members, they are split in different ratios into test and training sets.

In step 120 many k-nearest neighbor (kNN) mini-classifiers (mCs) that use the training set as their reference set are constructed using subsets of features. All classifiers described in this report use k=9 and use only mCs with single features (s=1) and pairs of features (s=2).

To target a final classifier that has certain performance characteristics, the mCs are filtered in step 126. This filtering is shown by the + and − signs 128 in FIG. 7A, with the + sign indicating that a particular mC passed filtering and a − sign indicating that a mC did not pass filtering. The filtering was as follows. Each mC is applied to its training set and performance metrics are calculated from the resulting classifications of the training set. Only mCs that satisfy thresholds on these performance metrics pass filtering to be used further in the process. The mCs that fail filtering are discarded. All classifiers presented in this document used filtering based on hazard ratios. For hazard ratio filtering, the mC is applied to its training set. The hazard ratio for a specified outcome (PFS or OS) is then calculated between the group classified as Early and the rest classified as Late. The hazard ratio must lie within specified bounds for the mC to pass filtering.

Combination of Mini-Classifiers Using Logistic Regression with Dropout (Step 130, 132)

Once the filtering of the mCs is complete, the mCs are combined into one master classifier (MC) in step 130 using a logistic regression trained on the training set class labels. To help avoid overfitting the regression is regularized using extreme drop out with only a small number of the mCs chosen randomly for inclusion in each of the logistic regression iterations. The number of dropout iterations is selected based on the typical number of mCs passing filtering to ensure that each mC is likely to be included within the drop out process multiple times. All classifiers presented in this report left in 10 randomly selected mCs per drop out iteration and used 10,000 dropout iterations. The resulting logistic regression weights for each mC over all of the dropout iterations were then averaged for definition of the master classifier.

We then evaluated the performance of the master classifier generated at step 130 by using it to classify the members of the test set 110.

Training/Test Splits (Loop 135)

The use of multiple training/test splits in loop 135 avoids selection of a single, particularly advantageous or difficult training set for classifier creation and avoids bias in performance assessment from testing on a test set that could be especially easy or difficult to classify.

At step 136 we optionally conduct an analysis of the data from each of the training/test set splits and get the performance characteristics for the MCs and their classification results for each split at step 138.

At step 144 we determine whether any of the samples in the development set persistently misclassify when they are in the test set (110). If so we flip the class label for such misclassified samples and via loop 146 repeat the process beginning at step 102 and continuing through steps 108, 120, 126 and 130 including looping over many different realizations of the training and test set split (loop 135).

Definition of Final Test 150 (FIG. 7B)

The output of the logistic regression that defines each MC generated at step 130 is a probability of being in one of the two training classes (Early or Late). Applying a threshold to this output produces a binary label (Early or Late) for each MC. For all classifiers presented in this report we used a cutoff threshold of 0.5. To select an overall final classification or test, a majority vote is done across all MCs ("ensemble average"). When classifying samples in the development set this is modified to incorporate in the majority vote only MCs where the sample is not in the training set ("out-of-bag majority vote").

For the definition of the final test, it is also possible to directly average the MC probabilities to yield one average probability for a sample. When working with the development set, this approach is adjusted to average over MCs for which a given sample is not included in the training set ("out-of-bag" estimate). These average probabilities can then be converted into a binary classification by applying a cutoff. Applying a cutoff of 0.5 to the averaged probabilities gives very similar classifications to using a cutoff of 0.5 on the individual MC probabilities and then performing the majority vote over the MCs. This approach was not used to produce the results shown in this document, however.

As another alternative, a final test could be defined at step 150 by simply selecting a MC for a particular training/test set split that has typical performance.

In the procedure of FIG. 7A-7B, it is preferable to perform a validation of the master classifier defined at step 150 on an independent sample set, as indicated at step 152. See the validation discussion below.

Figure 12:
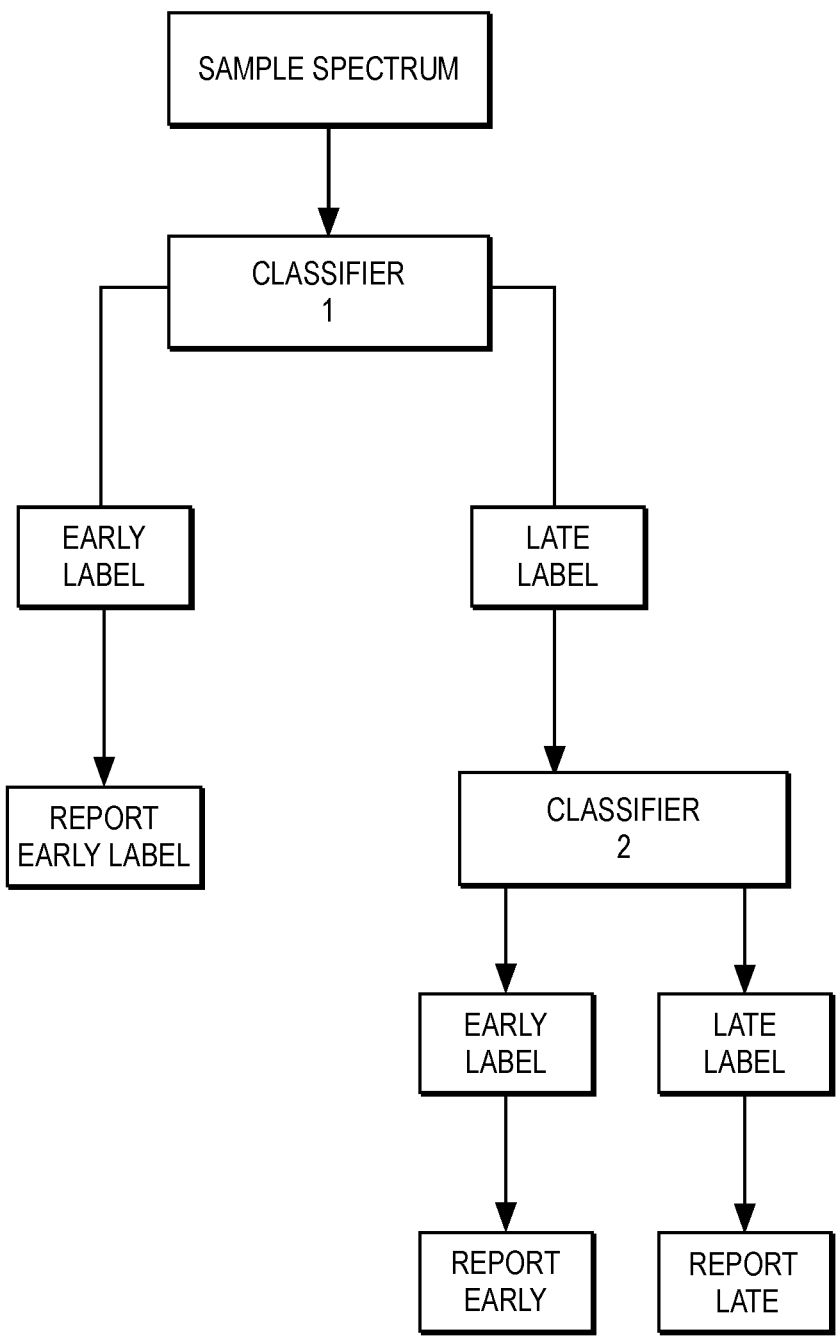
FIG. 12 illustrates a schema or hierarchical manner of defining a test using Classifier 1 and Classifier 2.

One embodiment of the melanoma/IL2 predictive test presented here uses a combination of two classifiers, Classifier 1 and Classifier 2, arranged in a hierarchical manner, see FIG. 12. The parameters and development set used to generate these classifiers are shown in Table 8. It will be appreciated that the methodology of FIG. 7A-7B was performed twice—for two different development sets as indicated in the Table 8, and for two different sets of mass spectrometry features, resulting in two different final classifiers defined at step 150. The two classifiers are used in a hierarchical manner as will be explained subsequently.

TABLE 8

| Parameters used for classifier development | | |
|---|---|---|
| | Classifier 1 | Classifier 2 |
| Development Set | All 114 samples and associated spectra | 70 samples and associated spectra classified as "Late" by Classifier 1 |
| k (for kNN classifiers) | 9 | 9 |
| # drop out iterations | 10,000 | 10,000 |
| # of mCs included in each drop out iteration | 10 | 10 |
| Features included in development | 22 (See Table 33) | All 326 (Table 32) with bagged feature deselection |
| Filtering criterion | HR for OS | HR for PFS |

Results

The IL2 test uses a hierarchy of two classifiers. The first classifier (Classifier 1) uses GSEA Acute Response features, i.e. the feature selection in FIG. 7A resulting in the feature space 50 was based on selection of a subset of all measured mass spectral features that were associated with acute response with GSEA p value of 0.05 or less. (The GSEA method and its use to find subgroups of mass spectral features associated with certain biological functions are described in Appendix D of our prior provisional application 62/369,289 filed Aug. 1, 2016 and the patent and technical literature cited previously). The application of GSEA to correlate mass spectral features with particular biological functions is also described at length in U.S. application Ser. No. 15/207,825 filed Jul. 12, 2016, and the relevant description of the procedure in that document is incorporated by reference herein.) The features are listed in Table 33. The classifier was developed on the whole set of 114 patients and gave classification labels of "Early" and "Late". The performance was assessed using Kaplan-Meier plots of OS and PFS between samples classified as Early and Late, together with corresponding hazard ratios (HRs) and log-rank p values. The results are summarized in tables 9-11 and the Kaplan-Meier plots of FIG. 8.

The Kaplan-Meier plots of overall survival (OS) and progression free survival (PFS) by early and late classification groups are shown in FIG. 8A-8B, respectively. FIGS. 8A-8B clearly shows that the samples in the development set classified as Early have relatively worse OS and PFS as compared to the samples classified as Late.

Second Classifier "Classifier 2"

The second classifier uses all features of Table 32 and then a bagged feature deselection step 52 (FIG. 7A, described in the patent literature cited previously, including US patent application publication 2016/0321561). The resulting list of features after feature deselection is listed in Table 33. The classifier was developed according to the procedure of FIGS. 7A-7B using as a development set 100 only the 70 samples that classified as Late with the Classifier 1. This classifier classified these 70 samples again as Early or Late. The results are summarized in tables 12-14 and in the Kaplan-Meier plots of FIGS. 9A-9B.

TABLE 9

Response characteristics by classification groups

|  | Early N = 44<br>n (%) | Late N = 70<br>n (%) |
|---|---|---|
| CR | 0 (0) | 8 (11) |
| PR | 7 (16) | 6 (9) |
| SD | 9 (20) | 17 (24) |
| PD | 26 (59) | 34 (49) |
| N/A | 1 (2) | 0 (0) |
| Minimal Response | 1 (2) | 5 (7) |

TABLE 10

Medians for time-to-event endpoints by classification group

|  | Median OS (95% CI) in days | Median PFS (95% CI) in days |
|---|---|---|
| Early | 596 (340-721) | 68 (49-86) |
| Late | 1105 (752-undefined) | 93 (72-149) |

TABLE 11

Survival analysis statistics between classification groups

|  | OS | | | PFS | | |
|---|---|---|---|---|---|---|
|  | log-rank p | CPH p | HR (95% CI) | log-rank p | CPH p | HR (95% CI) |
| Early vs Late | 0.001 | 0.001 | 2.38 (1.44-3.94) | 0.009 | 0.009 | 1.71 (1.14-2.57) |

TABLE 12

Response characteristics by classification groups

|  | Early N = 31<br>n (%) | Late N = 39<br>n (%) |
|---|---|---|
| CR | 0 (0) | 8 (21) |
| PR | 3 (10) | 3 (8) |
| SD | 8 (26) | 9 (23) |
| PD | 18 (58) | 16 (41) |
| N/A | 0 (0) | 0 (0) |
| Minimal Response | 2 (6) | 3 (8) |

TABLE 13

Medians for time-to-event endpoints by classification group

|  | Median OS (95% CI) in days | Median PFS (95% CI) in days |
|---|---|---|
| Early | 1094 (597-undefined) | 84 (50-127) |
| Late | 1193 (685-undefined) | 147 (77-331) |

TABLE 14

Survival analysis statistics between classification groups

| | OS | | | PFS | | |
|---|---|---|---|---|---|---|
| | log-rank p | CPH p | HR (95% CI) | log-rank p | CPH p | HR (95% CI) |
| Early vs Late | 0.738 | 0.739 | 1.13 (0.56-2.29) | 0.012 | 0.014 | 1.95 (1.15-3.30) |

The Kaplan-Meier plots of FIGS. 9A-9B of OS and PFS by classification group show that the Early and Late groups have similar OS, but in the PFS plot those samples which classify as Early have relatively worse PFS as compared to the samples which classify as Late.

Hierarchical Combination of Classifier 1 and 2 (FIG. 12).

The combined classifier uses the classification "Early" from the first classifier and then both "Early" and "Late" classification labels from the second classifier. If an Early label is generated by either Classifier 1 or Classifier 2, the Early label is reported. If the Late label is generated by Classifier 2, the Late label is reported, as per FIG. 12. In Tables 15-17 and in FIG. 10, Early and Late are the reported class labels as just described. The performance was assessed using Kaplan-Meier plots of OS and PFS between samples classified as Early and Late, together with corresponding hazard ratios (HRs) and log-rank p values. The results are summarized in tables 15-17 and FIGS. 10A-10B.

TABLE 15

Response characteristics by classification groups

| | Early N = 75<br>n (%) | Late N = 39<br>n (%) |
|---|---|---|
| CR | 0 (0) | 8 (21) |
| PR | 10 (13) | 3 (8) |
| SD | 17 (23) | 9 (23) |
| PD | 44 (59) | 16 (41) |
| N/A | 1 (1) | 0 (0) |
| Minimal Response | 3 (4) | 3 (8) |

TABLE 16

Medians for time-to-event endpoints by classification group

| | Median OS (95% CI) in days | Median PFS (95% CI) in days |
|---|---|---|
| Early | 653 (557-852) | 70 (57-86) |
| Late | 1193 (685-undefined) | 147 (77-331) |

TABLE 17

Survival analysis statistics between classification groups

| | OS | | | PFS | | |
|---|---|---|---|---|---|---|
| | log-rank p | CPH p | HR (95% CI) | log-rank p | CPH p | HR (95% CI) |
| Early vs Late | 0.036 | 0.038 | 1.81 (1.03-3.16) | 0.001 | 0.001 | 2.12 (1.36-3.30) |

Figure 10A:
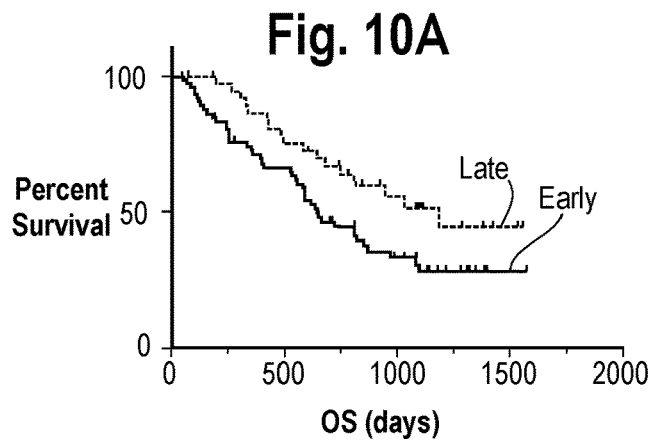
FIGS. 10A and 10B illustrate Kaplan-Meier plots of OS (FIG. 10A) and PFS (FIG. 10B) by classification groups Early and Late produced by a combination of Classifiers 1 and 2.
Figure 10B:
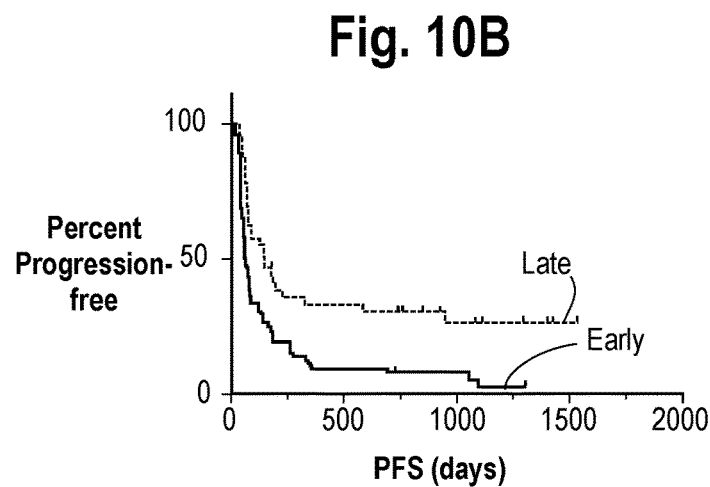

FIGS. 10A-10B illustrates the Kaplan-Meier plots of OS and PFS, respectively, by classification group for a classifier configured as a hierarchical combination of classifiers 1 and 2 as depicted in FIG. 12.

Note that the Early samples have significantly worse OS and PFS as compared to the samples classified as Late.

Similar results can be obtained by applying Classifier 2 to all samples in the cohort and using just the classification produced by Classifier 2, rather than the stacked or hierarchical approach of FIG. 12. This produces only three changes in label for samples that were classified by Classifier 1 as Early but classified by Classifier 2 as Late (one with progressive disease (PD), one with stable disease (SD), one with partial response (PR)). The results obtained from applying Classifier 2 alone to all 114 samples are shown in the Kaplan-Meier plots of FIGS. 11A-11B and tables 18-20.

TABLE 18

Response characteristics by classification groups

| | Early N = 72<br>n (%) | Late N = 42<br>n (%) |
|---|---|---|
| CR | 0 (0) | 8 (19) |
| PR | 9 (13) | 4 (10) |
| SD | 16 (22) | 10 (23) |
| PD | 43 (60) | 17 (40) |
| N/A | 1 (1) | 0 (0) |
| Minimal Response | 3 (4) | 3 (7) |

TABLE 19

Medians for time-to-event endpoints by classification group

| | Median OS (95% CI) in days | Median PFS (95% CI) in days |
|---|---|---|
| Early | 647 (537-852) | 68 (56-86) |
| Late | 1193 (752-undefined) | 147 (77-202) |

TABLE 20

Survival analysis statistics between classification groups

| | OS | | | PFS | | |
|---|---|---|---|---|---|---|
| | log-rank p | CPH p | HR (95% CI) | log-rank p | CPH p | HR (95% CI) |
| Early vs Late | 0.020 | 0.023 | 1.90 (1.09-3.28) | 0.001 | 0.002 | 2.00 (1.30-3.08) |

Figure 11A:
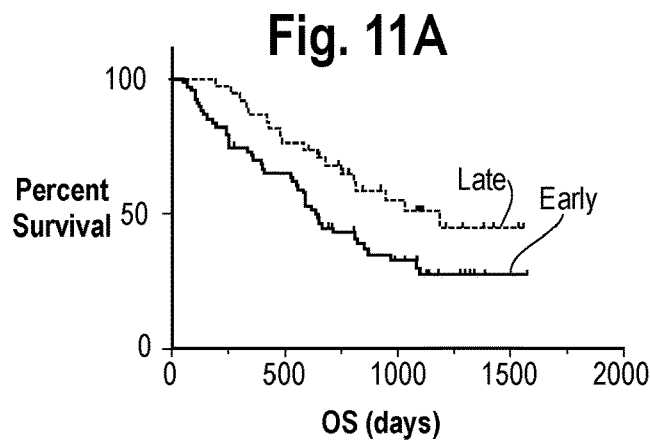
FIGS. 11A and 11B illustrate Kaplan-Meier plots of OS (FIG. 11A) and PFS (FIG. 11B) by classification groups Early and Late produced by the Classifier 2 described below when classifying all the 114 samples in the development set.
Figure 11B:
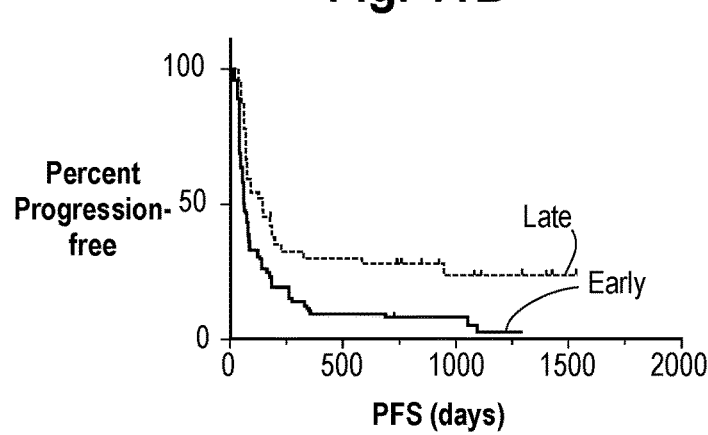

FIGS. 11A-11B shows the Kaplan-Meier plots of OS and PFS by classification group produced by the Classifier 2 on the whole set of 114 samples. Again note the clear separation in the Early and Late groups, with the Early groups having relatively worse OS and PFS as compared to the Late group.

Hence, in view of the above, there are several embodiments of practical classifiers and tests for melanoma patient benefit from IL2, namely either the hierarchical combination of Classifiers 1 and 2 as per FIG. 12, or just Classifier 2 alone.

Table 34 lists the class labels assigned to the 114 samples in the development sample set by the combination of Classifier 1 and Classifier 2 as per FIG. 12.

Reproducibility

To assess test reproducibility Classifier 1 and Classifier 2 were run on two sets of spectra generated from 119 samples collected from patients with advanced melanoma. The two sets of spectra were produced using independent sample preparation and spectral acquisition several weeks apart. Spectral acquisition and sample preparation procedures were identical to those described above The results obtained for the spectra for Classifier 1 and Classifier 2 were combined to produce an overall classification for each sample for each run and the results compared to assess test reproducibility in table 21. Label concordance between the two runs was 97%.

TABLE 21

Test reproducibility (Combination of Classifier 1 and Classifier 2)

| | | First Run | |
|---|---|---|---|
| | | Early | Late |
| Second Run | Early | 80 | 2 |
| | Late | 2 | 35 |

Biological Interpretation

Gene set enrichment analysis methods were used to examine the association of various biological processes with the test classifications. Details of the method are given in the patent and technical literature cited previously, see also Appendix D of our prior provisional application 62/369,289 filed Aug. 1, 2016, see also pages 106-146 of pending U.S. application Ser. No. 15/207,825 filed Jul. 12, 2016, and Appendix K of U.S. provisional application Ser. No. 62/289,587 filed Feb. 1, 2016, the content of which is incorporated by reference herein. Table 22 shows the univariate p values for the association of the biological processes with test classifications in an independent sample set of 49 samples for which matched deep MALDI spectra and protein panel data were available. No corrections were made for multiple testing. Note that for these 49 samples the results of the combination of Classifier 1 and Classifier 2 results and the results of simply taking the classifications of Classifier 2 for all samples are identical.

TABLE 22 p values from GSEA of association of test classifications with biological processes

| ProteinSetDescription | Enrichment Score (definition 1) | p-value |
|---|---|---|
| Acute inflammatory response | 0.501 | <0.001 |
| Activation of innate immune response | 0.332 | 0.733 |
| Regulation of adaptive immune response | 0.324 | 0.596 |
| Positive regulation of glycolytic process | −0.651 | 0.059 |
| Immune T-cells | 0.181 | 0.904 |
| Immune B-cells | −0.362 | 0.329 |
| Cell cycle regulation | −0.268 | 0.379 |
| Natural killer regulation | −0.180 | 0.979 |
| Complement system | 0.625 | 0.001 |
| Cancer-experimental | 0.718 | 0.575 |
| Acute response | 0.512 | 0.126 |
| Cytokine activity | −0.254 | 0.534 |
| Wound healing | −0.466 | 0.011 |
| Interferon | 0.170 | 0.959 |
| Interleukin-10 | 0.212 | 0.558 |
| Growth factor receptor signaling | −0.293 | 0.053 |
| Immune response | 0.278 | 0.065 |
| Immune Response Type 1 | 0.408 | 0.538 |
| Immune Response Type 2 | 0.560 | 0.378 |
| Immune Response-Complement | −0.176 | 0.847 |
| Immune Response-Complement-Acute Response | −0.204 | 0.580 |
| Acute phase | 0.597 | 0.004 |
| Hypoxia | −0.262 | 0.551 |
| Cancer | −0.182 | 0.673 |
| Cell adhesion | 0.216 | 0.569 |
| Mesenchymal transition | −0.325 | 0.704 |
| Extracellular matrix-restricted source, UNIPROT | −0.387 | 0.216 |
| Extracellular matrix-from different sources | −0.256 | 0.523 |
| Angiogenesis | −0.239 | 0.529 |

Acute inflammatory response, complement system, acute phase, and wound healing showed associations with test classifications at the $p<0.05$ significance level.

It is possible to present running sum plots used in the GSEA and the proteins from the biological process protein sets in the leading edges of these plots, using the methods described at pages 128-129 in our prior patent application Ser. No. 15/207,825 filed Jul. 12, 2016 and the paper of Subramanian et al. We created such plots of the running sum for the four biological processes identified as having meaningful associations with test classifications, namely: acute response, complement system, wound healing and acute phase. Tables 35-38 show the proteins in the leading edges of the running sums for acute response, complement system, wound healing, and acute phase and their individual correlations with test classifications Early and Late in this work.

Conclusions

Using deep MALDI-TOF mass spectra obtained from pre-treatment serum samples taken from patients receiving IL2 therapy for advanced melanoma we were able to use the Diagnostic Cortex (FIGS. 7A-7D) to create a test able to define a subset of patients (class label Late) where 21% experienced complete response, compared with only 7% in the unselected cohort, i.e. a tripling of complete response rate. This enrichment of very good outcomes in the "Late" classification group of the overall test based on a hierarchical combination of Classifier 1 and Classifier 2 (i.e. "Late" classification produced from Classifier 1 and a "Late" classification produced from Classifier 2) greatly increases the relative risk/cost to benefit ratio of IL2 therapy and would help to maintain it as or raise it to an attractive option for first-line therapy for patients with advanced melanoma whose serum is classified as "Late".

The test showed good reproducibility of 97% classification concordance in an independent cohort of 119 melanoma patients.

Gene set enrichment analyses showed that test classifications are associated with the biological functions acute phase, acute inflammatory response, complement system and wound healing. This is consistent with previous observations that high pre-treatment levels of CRP and IL-6 are associated with lack of response to IL2 therapy. In addition, some mass spectral features used in Classifier 2 have been tentatively identified as proteins associated with acute phase response (m/z 23049—C reactive protein (CRP), m/z 11686—serum amyloid A).

Validation of IL-2 Classifier on Independent Sample Set

We conducted a validation exercise on the IL2 test described above to samples collected prior to treatment of advanced melanoma patients treated with IL2 with or without stereotactic body radiation therapy (SBRT).

The IL2 test was developed on 114 pretreatment serum samples from the IL2Select study in collaboration with Drs. Ryan Sullivan (Massachusetts General Hospital Cancer Center) and David McDermott (Beth Israel Hospital). The goal of this development was to identify a patient subpopulation enriched for high dose IL2 benefit, in particular containing most of the complete responders (CRs). The results of this work indicated that it is possible to find a group of patients, i.e., those that serum has a Late label under the IL2 test, which contained all the CRs of subjects with available samples. The durable response rate at 1000 days follow-up in this group was 25%.

The purpose of this study was to evaluate the performance of this test in an independent blinded cohort. As the size of this set is small, and because there are differences in treatment through the addition of radiation therapy this study is exploratory.

Patients and Samples

Samples were available for 37 patients. Baseline characteristics for the cohort are summarized in table 23.

TABLE 23

Baseline characteristics of the cohort

| Attribute | | Median (Range) |
|---|---|---|
| Age | | 55 (20-76) |
| Baseline LDH | | 219 (124-1984) |
| Attribute | | n(%) |
| Baseline LDH | <ULN | 27 (73) |
| | ≥ULN | 10 (27) |
| ECOG PS | 0 | 25 (68) |
| | 1 | 11 (30) |
| | 2 | 1 (3) |
| Gender | Female | 9 (24) |
| | Male | 28 (76) |
| Prior SBRT | Yes | 19 (51) |
| | No | 18 (49) |
| Prior Interferon | Yes | 8 (22) |
| | No | 29 (78) |
| Any prior therapy | Yes | 22 (59) |
| | No | 15 (41) |

TABLE 23-continued

| Any prior therapy | Yes | 11 (30) |
|---|---|---|
| Except SBRT | No | 26 (70) |
| Prior Ipilimumab | Yes | 2 (5) |
| | No | 35 (95) |

Figure 20:
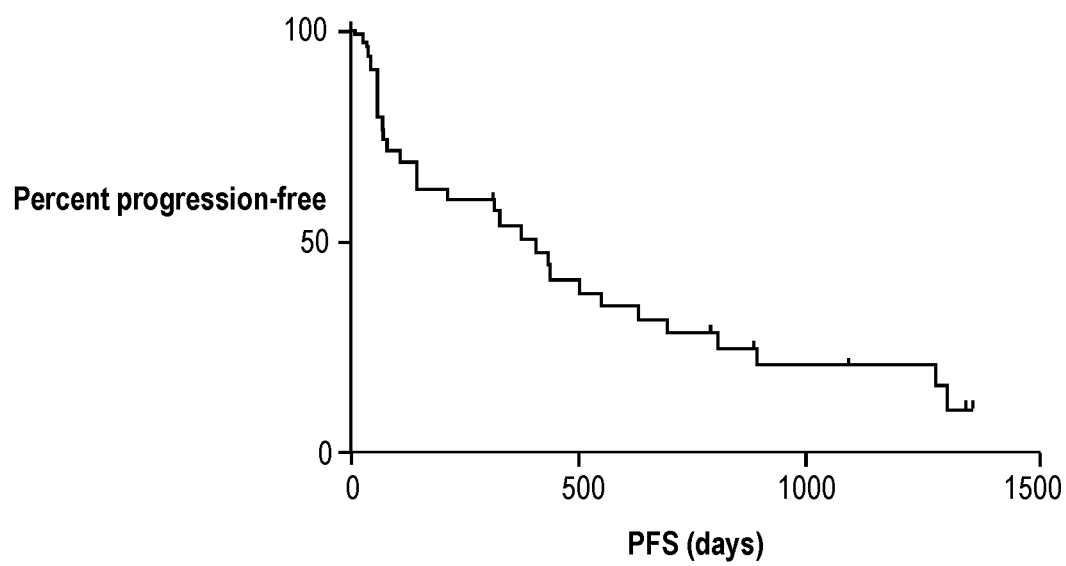
FIG. 20 is plot of PFS of a cohort of patients used for validation of the IL2 classifier.

The Kaplan-Meier plot of progression-free survival (PFS) for the entire cohort is shown in FIG. 20 and best response is summarized in table 24. Note that PFS information was not available for two patients, and so these were censored for PFS at day 1.

TABLE 24

Best response for the analysis cohort

| | n (%) |
|---|---|
| CR | 6 (16) |
| PR | 9 (24) |
| SD | 6 (16) |
| PD | 16 (43) |

Results

Twenty one (57%) of the samples classified as IL2 test Early and the remaining 16 (43%) classified as IL2 test Late.

Best response is summarized by test classification in table 25. Five of the six complete responses are in the Late classification group. (Fisher's exact test p for CR vs no CR=0.066; Fisher's exact test p for response (CR+PR vs SD+PD)=0.107.

TABLE 25

Best response by test classification

| | Early n(%) | Late n(%) |
|---|---|---|
| CR | 1 (5) | 5 (31) |
| PR | 5 (24) (PFS events at 208 days, 690 days, and 1274 days, censored at 780 days and 1078 days) | 4 (25) (PFS events at 369 days, 431 days, and 498 days, censored at 1351 days) |
| SD | 4 (19) | 2 (13) |
| PD | 11 (52) | 5 (31) |

Figure 21:
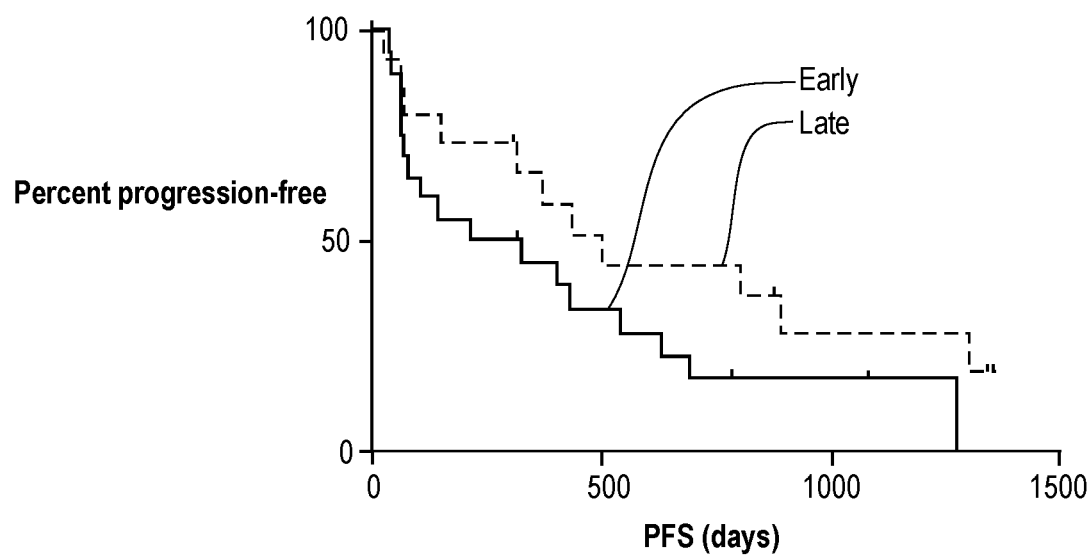
FIG. 21 is a Kaplan-Meier plot of PFS by IL2 test classification for the validation cohort.

FIG. 21 is a Kaplan-Meier plot of PFS by IL2 test classification. Statistics are shown in Table 26.

TABLE 26

Progression-free survival analysis statistics

| | Early (n = 21) | Late (n = 16) |
|---|---|---|
| Median PFS (95% CI) | 265 (59-543) | 498 (65-1300) |
| HR (95% CI) | 0.54 (0.24-1.19) | |
| log-rank p value | 0.121 | |
| Cox p value | 0.127 | |

Patient characteristics are summarized by test classification in Table 27.

TABLE 27

Baseline characteristics by test classification

| Attribute | | Early | Late | P value |
|---|---|---|---|---|
| Age | Median (Range) | 57 (30-71) | 52 (20-76) | 0.688* |
| Baseline LDH | | 263 (126-1984) | 210 (124-403) | 0.082* |

| Attribute | | n(%) | n(%) | |
|---|---|---|---|---|
| Baseline LDH | <ULN | 12 (57) | 15 (94) | 0.023 |
| | ≥ULN | 9 (43) | 1 (6) | |
| ECOG PS | 0 | 11 (52) | 14 (88) | 0.073** |
| | 1 | 9 (43) | 2 (13) | |
| | 2 | 1 (5) | 0 (0) | |
| Gender | Female | 4 (19) | 5 (31) | 0.458 |
| | Male | 17 (81) | 11 (69) | |
| Prior SBRT | Yes | 10 (48) | 9 (56) | 0.743 |
| | No | 11 (52) | 7 (44) | |
| Prior Interferon | Yes | 2 (10) | 6 (38) | 0.055 |
| | No | 19 (90) | 10 (63) | |
| Any prior therapy | Yes | 12 (57) | 10 (63) | >0.999 |
| | No | 9 (43) | 6 (38) | |
| Any prior except SBRT | Yes | 5 (24) | 6 (38) | 0.475 |
| | No | 16 (76) | 10 (63) | |
| Prior Ipilimumab | Yes | 2 (10) | 0 (0) | 0.496 |
| | No | 19 (90) | 16 (100) | |

*Mann-Whitney,
**Chi-squared, all others-Fisher's exact

Within this cohort test classification is significantly associated with baseline LDH (cutoff set to ULN=333 IU/L) and shows a trend to association with prior interferon treatment and performance status.

Table 28 shows the results of multivariate analysis of PFS, including covariates found to have at least a trend to association with test classification.

TABLE 28

Multivariate analysis of PFS including test classification, performance status, baseline LDH level, and prior interferon treatment

| | HR (95% CI) | p value |
|---|---|---|
| Test classification (Early vs Late) | 0.64 (0.25-1.64) | 0.354 |
| ECOG PS (0 vs 1 or 2) | 1.38 (0.60-3.17) | 0.453 |
| LDH (<ULN vs ≥ULN) | 2.68 (1.05-6.86) | 0.040 |
| Prior Interferon (No vs Yes) | 1.74 (0.67-4.53) | 0.258 |

The hazard ratio between Early and Late test classifications is somewhat increased (i.e., somewhat smaller effect size) in multivariate analysis, with the main effect coming from the inclusion of LDH into the analysis, likely due to the fact that all but one patient classified as Late in this small cohort had high baseline LDH. It should be noted that in the larger cohort of patients from Moffitt Cancer Center used for the development of the immunotherapy test of our prior patent application Ser. No. 15/207,825 filed Jul. 12, 2016, the majority of whom had already received at least one prior systemic treatment, many with ipilimumab, baseline LDH was generally much higher and 78% of patients classified as IL2 test Late had LDH greater than ULN.

This validation exercise supports the following conclusions:

1. Application of the IL2 test to samples from the trial of high dose IL2 with or without SBRT produced 43% "Late" classifications, in line with the proportion of 37% in samples used for the development of the IL2 test.

2. Five of the six patients with complete response we assigned a "Late" classification, raising the CR rate from 16% in the unselected population to 31% in the "Late" subgroup. Partial responses were split between both classification groups and response rate was numerically, but not statistically significantly larger in the Late group (56%) than in the Early group (29%), as may be expected given the size of the cohort.

3. The hazard ratio for PFS was somewhat larger than (HR=0.54), but not inconsistent with what had been found in the development cohort (HR=0.47).

4. Further validation of test performance, including investigation of effect size when adjusted for known prognostic factors, in larger cohorts is required.

Within the limits of this small validation cohort, the performance of the IL2 test was consistent with results found in the development cohort. The test was able to enrich the proportion of complete responders and overall responders from 16% and 41%, respectively, in the unselected population to 31% and 56%, respectively, in the good prognosis subgroup.

C. Practical Testing System (FIG. 13)

Once the classifier or classifiers as described above have been developed, their parameters and reference sets can now be stored and implemented in a general purpose computer and used to generate a class label for a blood-based sample, e.g., in accordance with the test described above. The class label can predict in advance whether a melanoma patient is likely to relatively benefit from high dose IL2 therapy, i.e., where the classifier (or classifiers) produce the Late class label or the equivalent.

Figure 13:
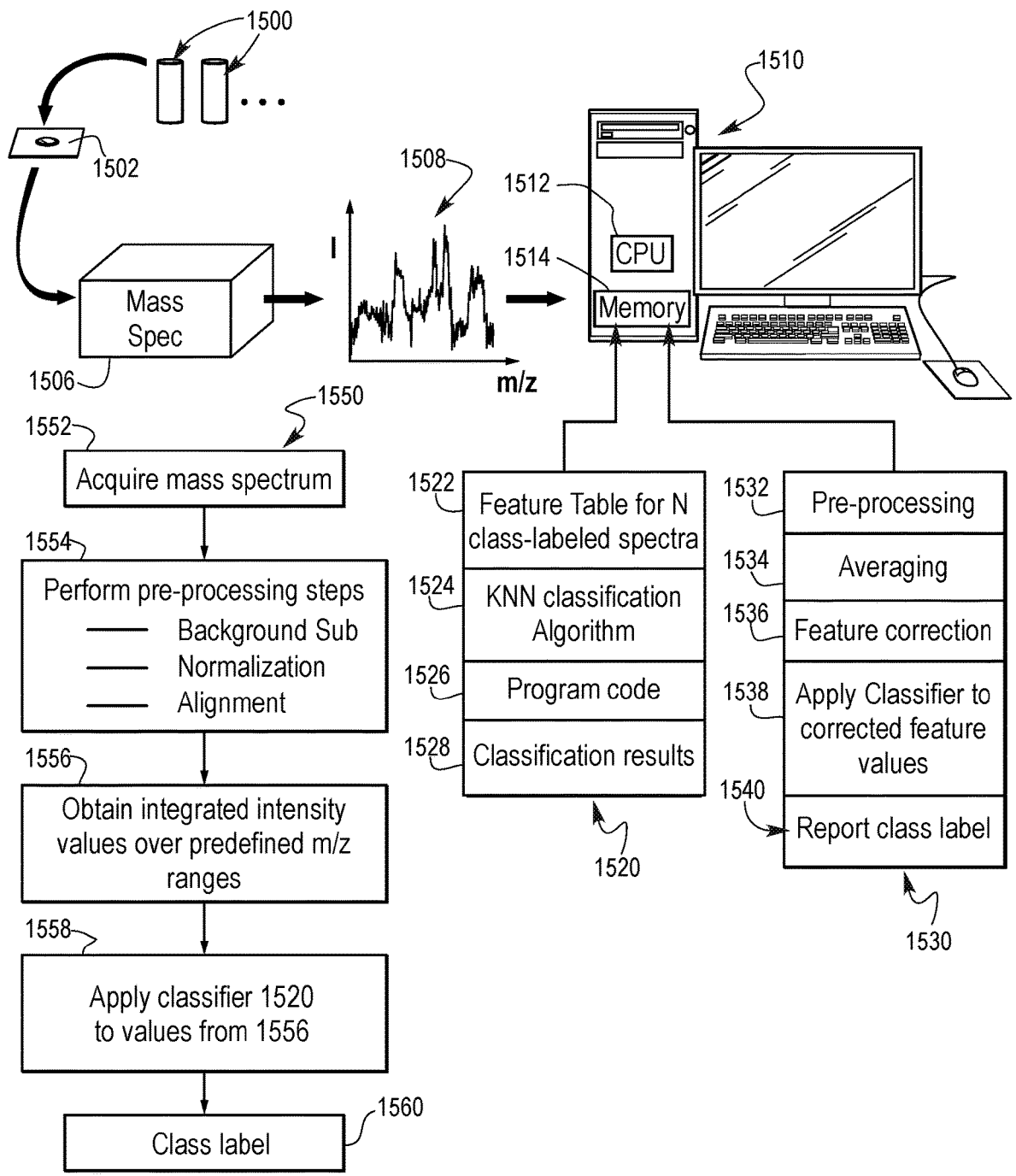
FIG. 13 is a block diagram of a practical testing environment for conducting a test on a blood-based sample from a melanoma patient to determine in advance of treatment whether they are likely to obtain relatively greater benefit from high dose IL2 in treatment of the cancer.

FIG. 13 is an illustration of a laboratory testing center or system for processing a test sample (in this example, a blood-based sample from a melanoma patient) using a classifier generated in accordance with FIG. 7A-7B. The system includes a mass spectrometer 1506 and a general purpose computer 1510 having CPU 1512 implementing a classifier 1520 coded as machine-readable instructions and a memory 1514 storing a reference mass spectral data set including a feature table 1522 of class-labeled mass spectrometry data. This reference mass spectral data set forming the feature table 1522 will be understood to be the mass spectral data (integrated intensity values of predefined features, see Table 33), associated with a development sample set to create the classifier resulting from procedure FIG. 7A-7B, or some subset thereof, e.g., the subset of patients who test Late by classifier 1 where the test uses classifier 2 alone. This data set could be from all the samples, e.g., for classifier 1, or a subset of the samples (e.g., the set for classifier 2), or both. It will be appreciated that the mass spectrometer 1506 and computer 1510 of FIG. 13 could be used to generate the classifier 1520 in accordance with the process of FIG. 7A-7B.

The operation of the system of FIG. 13 will be described in the context of conducting a predictive test for predicting melanoma patient benefit from high dose IL2 therapy. The following discussion assumes that the classifier 1520 is already generated at the time of use of the classifier to generate a class label (Early or Late, or the equivalent) for a test sample.

The system of FIG. 13 obtains a multitude of samples 1500, e.g., blood-based samples (serum or plasma) from diverse cancer (e.g., melanoma) patients and generates a class label for the samples as a fee-for-service. The samples 1500 are used by the classifier 1520 (implemented in the computer 1510) to make predictions as to whether the patient providing a particular sample is likely or not likely to benefit from high dose IL2 therapy. The outcome of the test is a binary class label such as Early or Late or the like which is assigned to the patient blood-based sample. The particular moniker for the class label is not particularly important and could be generic such as "class 1", "class 2" or the like, but as noted earlier the class label is associated with some clinical attribute relevant to the question being answered by the classifier. As noted earlier, in the present context the Early class label is associated with a prediction of relatively less benefit (e.g. overall survival or progression free survival), and the Late class label is associated with a prediction of relatively greater benefit (e.g., relatively longer overall survival or progression free survival).

The samples may be obtained on serum cards or the like in which the blood-based sample is blotted onto a cellulose or other type card. Aliquots of the sample are spotted onto one or several spots of a MALDI-TOF sample "plate" 1502 and the plate inserted into a MALDI-TOF mass spectrometer 1506. The mass spectrometer 1506 acquires mass spectra 1508 from each of the spots of the sample. The mass spectra are represented in digital form and supplied to a programmed general purpose computer 1510. The computer 1510 includes a central processing unit 1512 executing programmed instructions. The memory 1514 stores the data representing the mass spectra 1508. Ideally, the sample preparation, spotting and mass spectrometry steps are the same as those used to generate the classifier in accordance with FIG. 7A-7B.

The memory 1514 also stores a data set representing classifier 1520, which includes a) a reference mass spectral data set 1522 in the form of a feature table of N class-labeled spectra, where N is some integer number, in this example a development sample set of spectra used to develop the classifier as explained above or some sub-set of the development sample set. The classifier 1520 includes b) code 1524 representing a kNN classification algorithm (which is implemented in the mini-classifiers as explained above), including the features and depth of the kNN algorithm (parameter s) and identification of all the mini-classifiers passing filtering, c) program code 1526 for executing the final classifier generated in accordance with FIG. 7 on the mass spectra of patients, including logistic regression weights and data representing master classifier(s) forming the final classifier, including probability cutoff parameter, mini-classifier parameters for each mini-classifier that passed filtering, etc., and d) a data structure 1528 for storing classification results, including a final class label for the test sample. The memory 1514 also stores program code 1530 for implementing the processing shown at 1550, including code (not shown) for acquiring the mass spectral data from the mass spectrometer in step 1552; a pre-processing routine 1532 for implementing the background subtraction, normalization and alignment step 1554 (details explained above), filtering and averaging of the 800 shot spectra at multiple locations per spot and over multiple MALDI spots to make a single 400,000+shot average spectrum (as explained above), a module (not shown) for calculating integrated intensity values at predefined M/z positions in the background subtracted, normalized and aligned spectrum (step 1556), and a code routine 1538 for implementing the final classifier 1520 using the reference dataset feature table 1522 on the values obtained at step 1556. The process 1558 produces a class label at step 1560. The module 1540 reports the class label as indicated at 1560 (i.e., "Early" or "Late" or the equivalent).

The program code 1530 can include additional and optional modules, for example a feature correction function code 1536 (described in U.S. patent application publication 2015/0102216) for correcting fluctuations in performance of the mass spectrometer, a set of routines for processing the spectrum from a reference sample to define a feature correction function, a module storing feature dependent noise characteristics and generating noisy feature value realizations and classifying such noisy feature value realizations, modules storing statistical algorithms for obtaining statistical data on the performance of the classifier on the noisy feature value realizations, or modules to combine class labels defined from multiple individual replicate testing of a sample to produce a single class label for that sample. Still other optional software modules could be included as will be apparent to persons skilled in the art.

The system of FIG. 13 can be implemented as a laboratory test processing center obtaining a multitude of patient samples from oncologists, patients, clinics, etc., and generating a class label for the patient samples as a fee-for-service. The mass spectrometer 1506 need not be physically located at the laboratory test center but rather the computer 1510 could obtain the data representing the mass spectra of the test sample over a computer network.

D. Other Classifiers Developed from Melanoma Patient Samples Treated with Antibody Drugs Targeting the Programmed Cell Death 1 (PD-1) Checkpoint Protein.

We have developed classifiers for predicting melanoma patient benefit from anti-PD-1 drugs including nivolumab. See U.S. provisional application Ser. No. 62/289,587 filed Feb. 1, 2016, the content of which is incorporated by reference herein, and U.S. application Ser. No. 15/207,825 filed Jul. 12, 2016. Example 1 of the '587 application and the '825 application describes a classifier, referred to herein as "IS2", which was developed from a cohort of 119 blood-based samples from melanoma patients in advance of treatment with nivolumab. The classifier was developed using the same procedure of FIG. 7A-7B. Mini-classifier filtering was performed on simple overall survival. The M/z features which were used for IS2 classifier generation are listed in Appendix A of the prior provisional application Ser. No. 62/289,587 and in the '825 application filed Jul. 12, 2016. The classifier was able to split the development set into Early and Late groups with the Late groups having improved OS and PFS on nivolumab. The Kaplan-Meier plots and statistics for the classifier performance are set forth in Example 1 of application Ser. No. 62/289,587 and Example 1 of the '825 application filed Jul. 12, 2016.

We also described in our prior provisional Ser. No. 62/289,587 filed Feb. 1, 2016, at pages 113-119 thereof, Example 5, the development of an ensemble of seven different classifiers, each of which are constructed from different subsets of the 119 melanoma/nivolumab patients samples with different proportions of patients with small and large tumors. This ensemble of classifiers is referred to herein as "IS6". The description of the ensemble of classifiers and how it was generated (using the procedure of FIG. 7A-7B for seven different development sets) is incorporated by reference herein.

Briefly, in the "IS6" classifier, the deep MALDI feature table for the pretreatment serum samples from melanoma patients treated with nivolumab at the Moffitt Cancer Center was used for classifier development. For classifier development, the 104 samples for the patients who had tumor size follow up data were used. These 104 samples were split into two groups according to baseline tumor size: the 50 patients with smallest tumors and the 54 patients with largest tumors. Each of these subsets was used as the development set to develop a classifier using the process of FIG. 7A-7B, with bagged feature deselection and filtering of mini-classifiers on overall survival.

In addition, five other subsets of the 104 sample classifier development set were defined as additional or alternative development sets. The first of these took the set of 50 patients with smallest tumors, dropped 10 of them, and replaced these with 10 patients from the set of 54 with the larger tumors. The second of these took the set of 50 patients with smallest tumors, dropped 20 of them, and replaced these with 20 patients from the set of 54. Three other development sets were defined extending this approach further. The fifth classifier was accordingly a subset of the original 54 large tumor size set. In this way, 5 development sets of 50 patient samples were generated that contained different proportions of patients with smaller and larger tumor sizes (80%-20%, 60%-40%, 40%-60%, 20%-80%, and 0%-100%, respectively). For each of these 5 development sets, classifiers were generated using the same procedure of FIG. 7A-7B described in detail above, i.e., each classifier was defined as a final classifier as an ensemble average over 625 master classifiers generated from 625 test/training splits of the development set used for that classifier, and each master classifier is a logistic regression combination of a multitude of mini-classifiers that pass overall survival performance filtering criteria, and regularized by extreme drop out. Each classifier produces a binary class label for a sample, either Early or Late, and Early and Late have the same clinical meaning as explained in Example 1 of the prior provisional application 62/289,587. Hence, we obtained an ensemble of 7 different classifiers (the 5 developed as described here, plus the "large" and "small" tumor classifiers described in the "Classifiers incorporating tumor size information" section), each of which was developed on a clinically different classifier development set. It will be noted that the "large" tumor classifier described in the "Classifiers incorporating tumor size information" section and the fifth of the new classifiers generated from 50 "large" tumor patients are similar, but distinct in that they were formed from different sets of patients.

An alternative method for defining the classifier development sets with different clinical groupings is as follows:
1. Order the 104 samples by tumor size.
2. Take the 50 samples with the smallest tumor size for one classifier development and the remaining 54 samples with the largest tumor for another, just as here.
3. Define 5 other classifier development sets by
   a. Dropping the 10 samples with the smallest tumor size and taking the next 50 samples for a classifier development set.
   b. Dropping the 20 samples with the smallest tumor size and taking the next 50 samples for a second classifier development set.
   c. Dropping the 30 samples with the smallest tumor size and taking the next 50 samples for a third classifier development set.
   d. Dropping the 40 samples with the smallest tumor size and taking the next 50 samples for a forth classifier development set.
   e. Dropping the 50 samples with the smallest tumor size and taking the next 50 samples for a fifth classifier development set.

Classifiers are then developed from each of these seven classifier development sets using the procedure of FIG. 7A-7B. One then establishes rules to combine the classification results from these seven classifiers. This method of designing classifier development sets may have similar performance as the classifiers produced from the development sets described in the previous paragraphs, but may be more reproducible, for example in a rerunning of the samples.

To conduct a test on a patient's blood-based sample, the sample is subject to mass spectrometry as described above in the description of FIG. 13. The resulting mass spectral data (integrated intensity values at the classification features used in the classifier development exercise) is then subject to classification by each of the 7 classifiers in the ensemble, using the general procedure of FIG. 13. Each of the 7 classifiers generates a class label (Early/Late or similar). The set of 7 class labels is used to define an overall classification for a test sample in accordance with a set of rules. In one particular example, samples where all classifiers in the ensemble return a good prognosis "Late" label are classified as "Good", samples where all classifiers return a poor prognosis "Early" label are classified as "Bad", and all other samples with mixed labels are classified as "Other". Of course, other monikers for this ternary class label scheme could be used and the particular choice of moniker is not particularly important. Other rules for combining the 7 labels could, of course, be used.

Thus, the IS6 classifier produces labels of Good, Bad and Other depending on how the sample is classified by the ensemble of seven tumor size classifiers as explained in the provisional application Ser. No. 62/289,587, Example 5.

In our prior provisional application 62/289,587 we described how the association with the complement system with the Early and Late class labels lead to further insights regarding the Example 1 classifier ("IS2", melanoma/nivolumab). In particular, the observed upregulation of the complement system proteins in the group classified as Early may indicate that these patients have higher levels of immunosuppression, and/or higher levels of pro-tumor inflammation, related to the activation of the corresponding immune checkpoints, and as a result are less responsive to such drugs as nivolumab, ipilimumab, pembrolizumab, or other agents targeting these pathways. Interestingly, it has been shown that the complement protein C5a promotes the expression of the PD-1 ligands, PD-L1 and PD-L2. Zhang, J. Immunol. 2009; 182: 5123-5130. In this scenario one could envision that excessive complement upregulation might compete with efforts to inhibit PD-1. On the other hand, the results of recent clinical trials suggest that patients with tumor microenvironment characterized by high expression of PDL1 and presence of Tregs are more likely to respond to anti-PD1, anti-CTLA 4, or high dose IL-2 therapy. Though we do not know how exactly upregulation of the complement system is correlated with Example 1 classifications, this connection is in line with the biological effects of the complement system discussed at pages 94-95 of our prior provisional application Ser. No. 62/289,587. Consequently, we can expect that Example 1 classifiers (IS2) may be relevant for the broad variety of drugs affecting the immunological status of the patient, such as various immune checkpoint inhibitors and high dose IL2.

In this section of the document we describe an exercise of performing a classification of the melanoma/IL2 sample set with the IS2 and IS6 classifiers, which reveals that the IS2 and IS6 classifiers can be useful alone and in conjunction with the IL2 classifier in guiding treatment of melanoma patients.

Spectra from two of the patients in the 114 patient melanoma/IL2 cohort described above failed quality control for IS2 and IS6 testing, leaving 112 patients with matched IS2, IS6 and IL2 test classifications. Correspondence of the classifications in this cohort is summarized in table 29.

TABLE 29

IS2, IS6, and IL2 test classifications for the IL2 test development cohort

| | | IL2 Test Early (N = 73) | IL2 Test Late (N = 39) |
|---|---|---|---|
| IS2 | Early (N = 23) | 23 | 0 |
| | Late (N = 89) | 50 | 39 |
| IS6 | Bad (N = 10) | 10 | 0 |
| | Other (N = 49) | 44 | 5 |
| | Good (N = 53) | 19 | 34 |

All samples that are IL2 test Late are IS2 Late and all samples that are IS6 Bad are IL2 Early.

Table 30 shows the breakdown of best response categories for each test classification. The partial responders are broken down by those with a PFS event prior to 1 year (8 patients), those with a PFS event after 1000 days (1 patient) and those still censored for PFS (4 patients). (No patients with a partial response had an event between 1 year and 1000 days.) All patients with a complete response remain progression-free.

TABLE 30

|  |  | PD | SD | Minimal Response | PR (PFS <1 yr, PFS > 1000 days, no PFS event) | CR | NA |
|---|---|---|---|---|---|---|---|
| IL2 Test | Early | 44 | 15 | 3 | 10 (7, 1, 2) | 0 | 1 |
|  | Late | 16 | 9 | 3 | 3 (1, 0, 2) | 8 | 0 |
| IS2 | Early | 16 | 3 | 0 | 4 (3, 1, 0) | 0 | 0 |
|  | Late | 44 | 21 | 6 | 9 (5, 0, 4) | 8 | 1 |
| IS6 | Bad | 7 | 0 | 0 | 3 (2, 1, 0) | 0 | 0 |
|  | Other | 29 |  | 3 | 5 (4, 0, 1) | 2 | 1 |
|  | Good | 24 | 15 | 3 | 5 (2, 0, 3) | 6 | 0 |

Figure 14A:
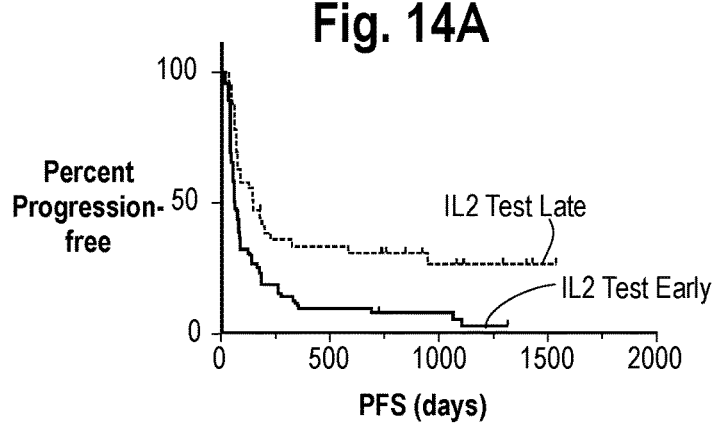
FIGS. 14A-14F are a set of Kaplan-Meier plots of PFS and OS for the 112 patients in the IL2 cohort showing classifications produced by the IL2 classifier of this disclosure (FIGS. 14A-14B) as well as classifications produced by the Example 1 and Example 5 classifiers ("IS2" and "IS6", respectively) of U.S. provisional application Ser. No. 62/289,587 filed Feb. 1, 2016, see FIGS. 14C-14F.
Figure 14B:
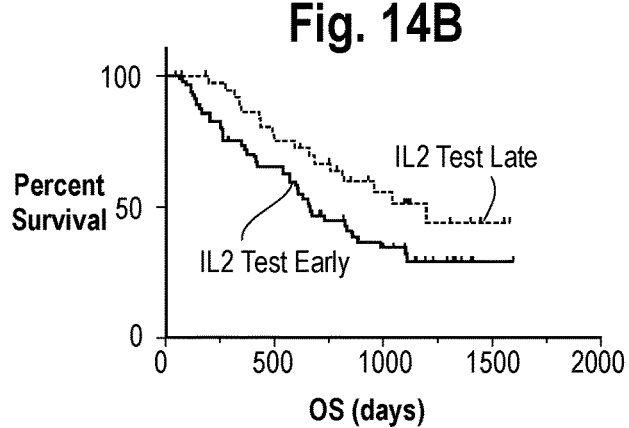
Figure 14C:
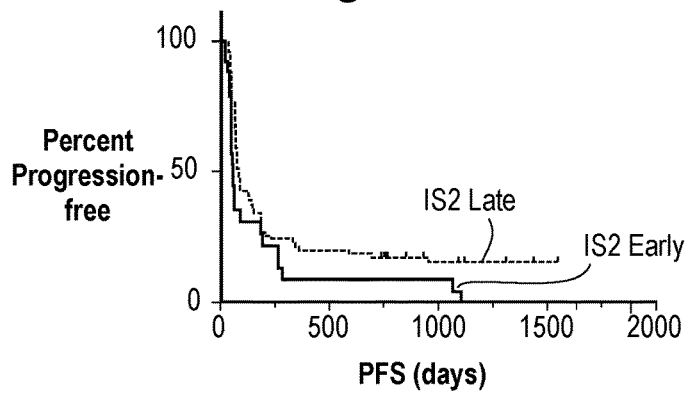
Figure 14D:
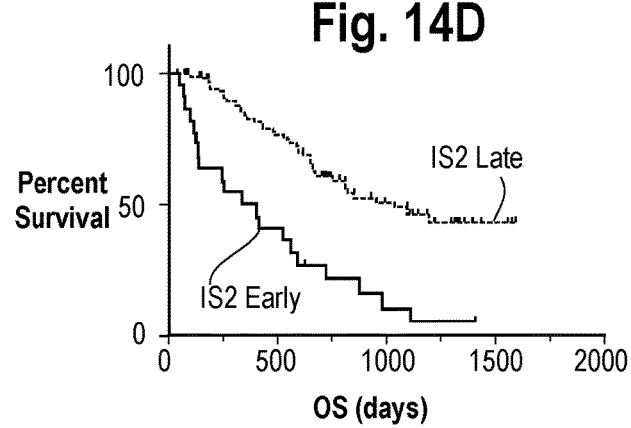
Figure 14E:
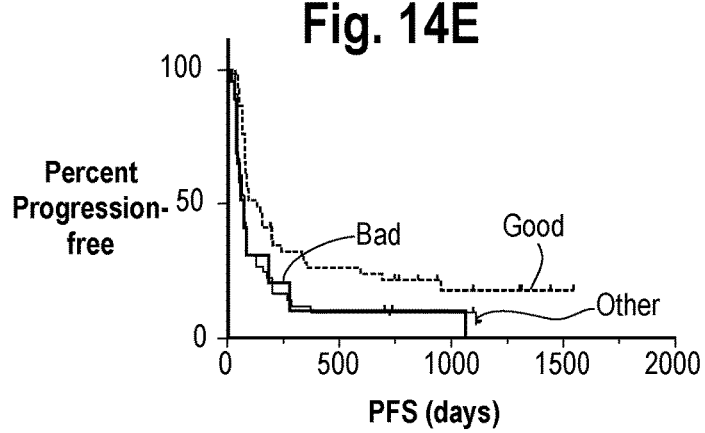
Figure 14F:
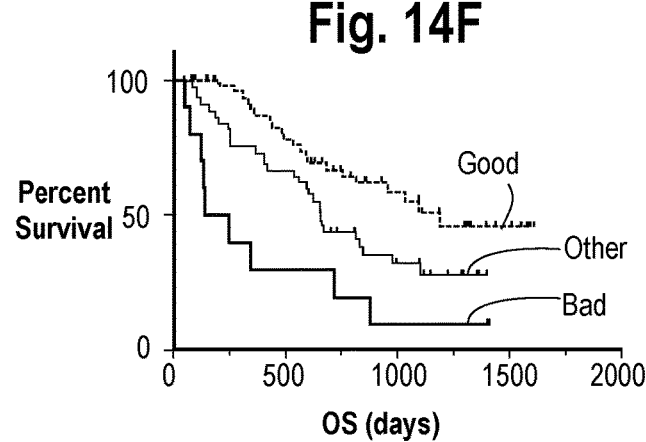

FIGS. 14A-14B shows the time-to-event outcomes by test classification for each test within the cohort of 112 patients with all 3 classifications. In terms of the table of responses and PFS, the IL2 test show clear superiority at identifying a group of patients who have a higher likelihood of a complete or long term durable response to IL2 therapy. The superior stratification power of IS2 and IS6 for OS prediction is believed to be due to likely subsequent treatment with checkpoint inhibitors in patients not showing a durable response to IL2.

Figure 15A:
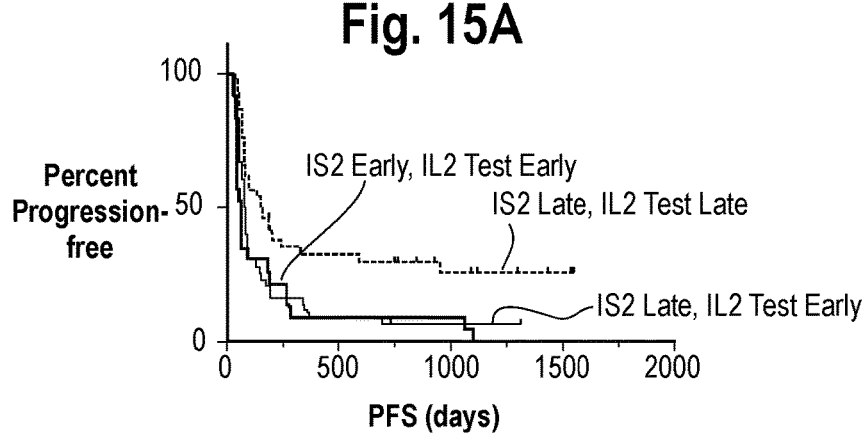
FIGS. 15A-15B show Kaplan-Meier plots of PFS (FIG. 15A) and OS (FIG. 15B) by combination of the IS2 and IL2 classifiers.
Figure 15B:
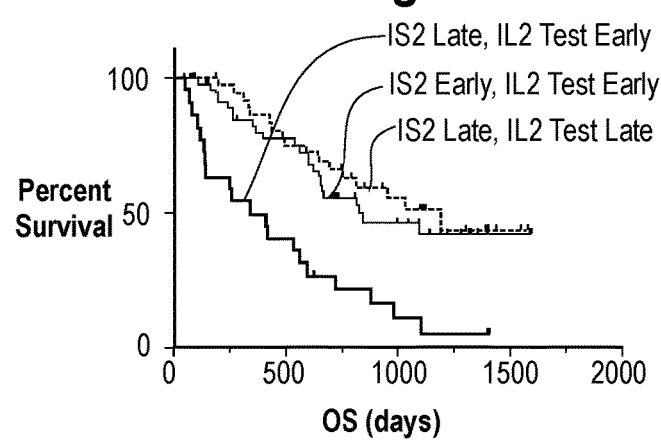

Breaking down by combination of IS2 and IL2 test classifications gives the Kaplan-Meier plots in FIG. 15A-15B. For PFS it is apparent that IS2 classification adds no predictive power to IL2 Test classification: all IL2 Test Late patients are IS2 Late and the PFS for IL2 Test Early patients is similar regardless of IS2 classification. For OS, however, IL2 classification adds no predictive power to IS2 classification: IS2 Late patients have similar OS regardless of whether they are IL2 Test Early or Late. The combination of these two results is consistent with the interpretation that IL2 Late patients perform well on IL2 therapy and the IS2 Late patients who are IL2 Early are able to make up for the markedly lower PFS by good performance on subsequent therapy, such as e.g., checkpoint inhibitors.

Figure 16A:
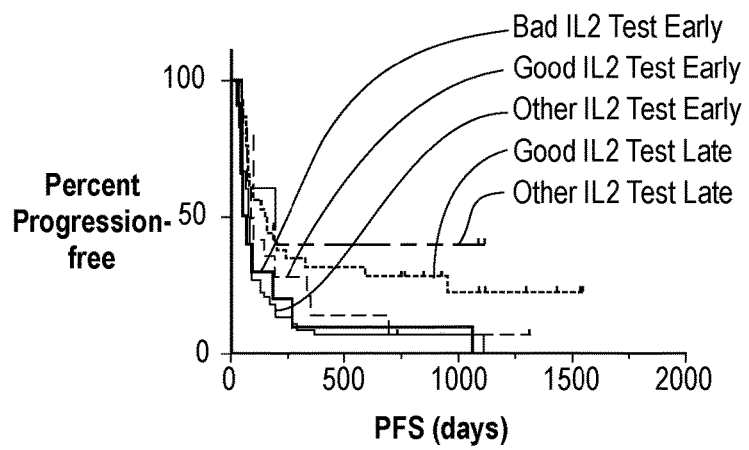
FIGS. 16A-16B show Kaplan-Meier plots of PFS (FIG. 16A) and OS (FIG. 16B) by combination of the IS6 and IL2 classifiers.
Figure 16B:
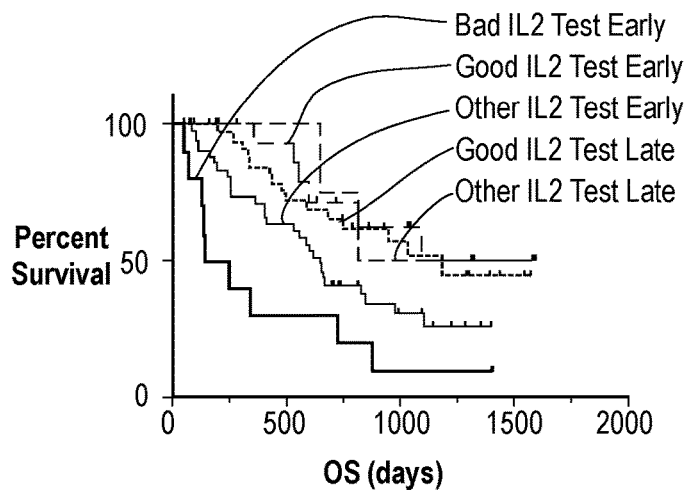

Breaking down by combination of IS6 and IL2 test classifications gives the Kaplan-Meier plots in FIGS. 16A-16B. The results bear a similar interpretation as for those for IS2 and IL2 test. For PFS, IS6 classification adds no additional information to IL2 test classification. For OS, patients with IL2 Test classification Late have similar outcome to patients classified as IS6 Good, while patients classified as IS6 Other or Bad and IL2 test Early have inferior survival.

These data are consistent with the IL2 test and IS2 and IS6 tests being able to identify a common group of patients who perform poorly on both IL2 therapy and anti-PD-1 therapy, while the IL2 test is able to isolate a group of patients (IL2 test Late) with good outcomes on IL2 and IS2 and IS6 are able to identify patients with good outcomes on other subsequent therapies (e.g. anti-PD-1). These two groups of good performing patients intersect, but are not the same. Apparently, patients who are classified as IL2 test Early who as a group have poor PFS on IL2 therapy can catch up with the superior performance of IL2 test Late patients on subsequent therapy if they are also classified as IS6 Good to obtain similar OS. These data are consistent with observations that patients treated with IL2 who do not achieve durable responses can have good outcomes on subsequent therapies.

We also performed a classification of the 119 patient samples which were used to develop the melanoma/nivolumab IS2 and IS6 classifiers (a cohort of samples referred to as "the Moffitt cohort") with the IL2, IS2 and IS6 classifiers. Correspondence of the classifications in this cohort is summarized in table 31.

TABLE 31

IS2, IS6, and IL2 test classifications for the Moffitt cohort

|  |  | IL2 Test Early (N = 82) | IL2 Test Late (N = 37) |
|---|---|---|---|
| IS2 | Early (N = 47) | 47 | 0 |
|  | Late (N = 72) | 35 | 37 |
| IS6 | Bad (N = 30) | 29 | 1 |
|  | Other (N = 55) | 46 | 9 |
|  | Good (N = 34) | 7 | 27 |

All samples that are IL2 test Late are IS2 Late and all samples but one (97%) that are IS6 Bad are IL2 Early.

Figure 17A:
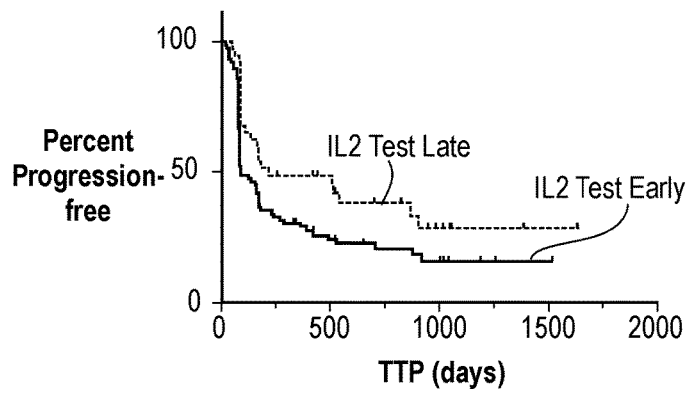
FIGS. 17A-17F are a set of Kaplan-Meier plots of TTP and OS for the 119 patients in a sample set referred to as "Moffitt Cohort", namely a set of melanoma patients treated with nivolumab, with classifications of this set of samples produced by the IL2 classifier (FIG. 17A-17B), the IS2 classifier (FIGS. 17C-17D) and the IS6 classifier (FIGS. 17E-17F).
Figure 17B:
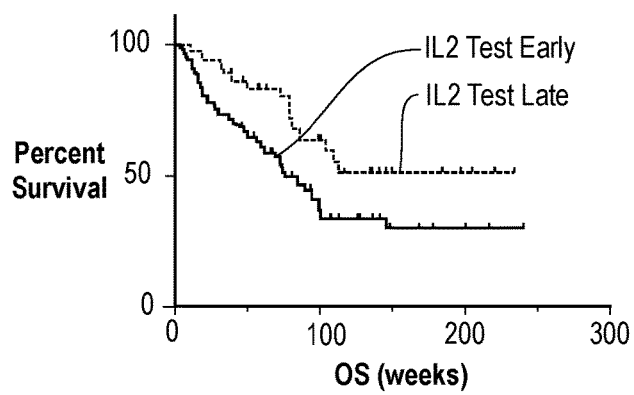
Figure 17C:
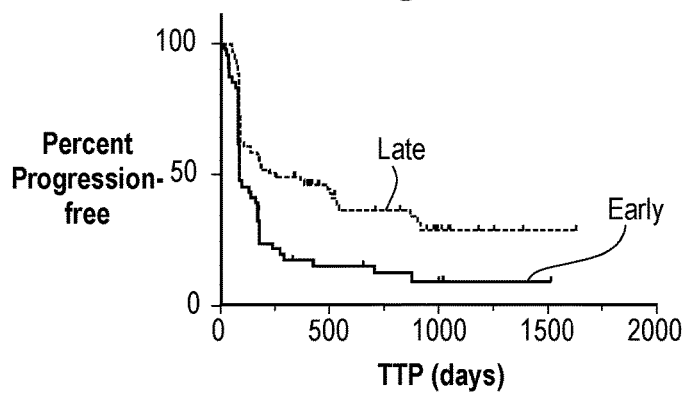
Figure 17D:
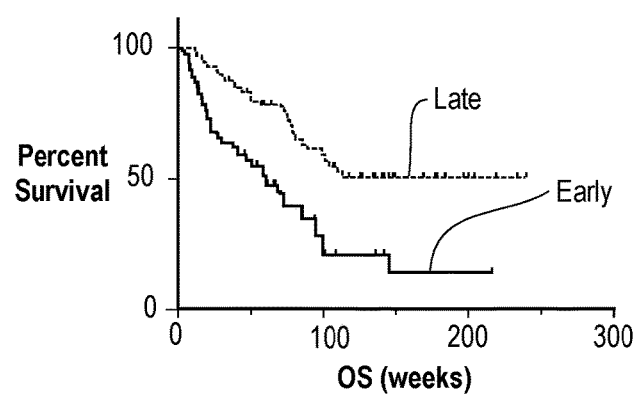
Figure 17E:
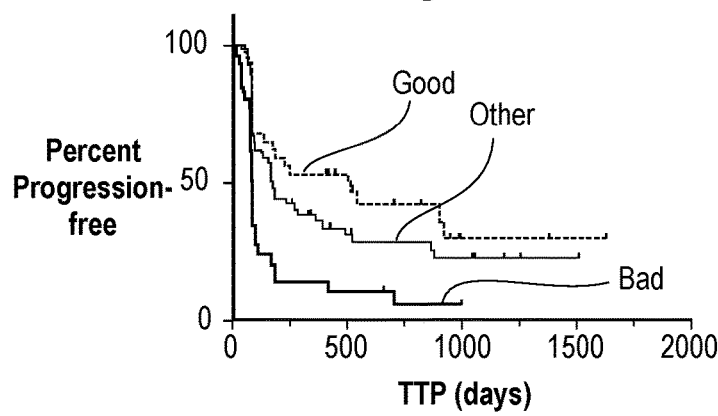
Figure 17F:
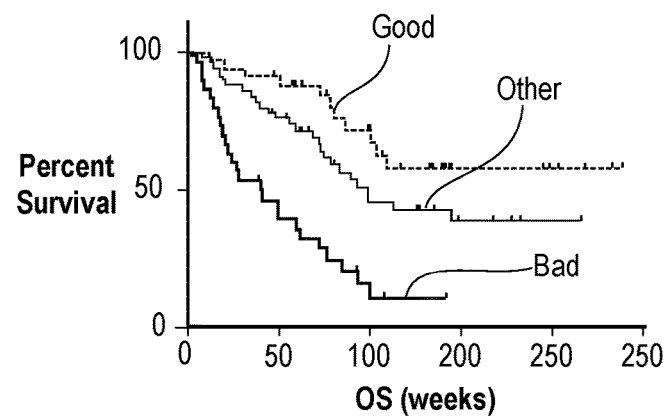

FIGS. 17A-17B shows the Kaplan-Meier plots of TTP and OS for the 119 patients in the Moffitt Cohort for each set of test classifications separately. While the IL2 test has some ability to stratify patients treated with nivolumab into groups with better and worse time-to-progression (TTP) and OS, its performance for both endpoints is inferior to the IS2 and IS6 tests. Note that it is unlikely that many patients in this study received IL2 therapy after the nivolumab study therapy (as generally IL2 is given as a first line therapy and use of IL2 in the era of anti-PD-1 therapy is decreasing).

Figure 18A:
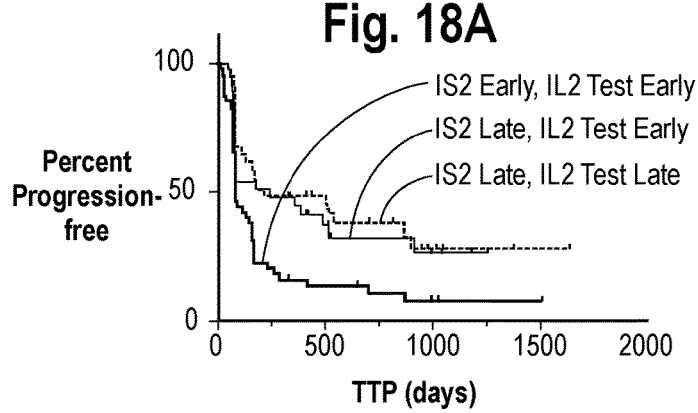
FIG. 18A-18B are Kaplan-Meier plots of TTP and OS (FIGS. 18A and 18B, respectively) by combination of the IS2 and IL2 classifiers.
Figure 18B:
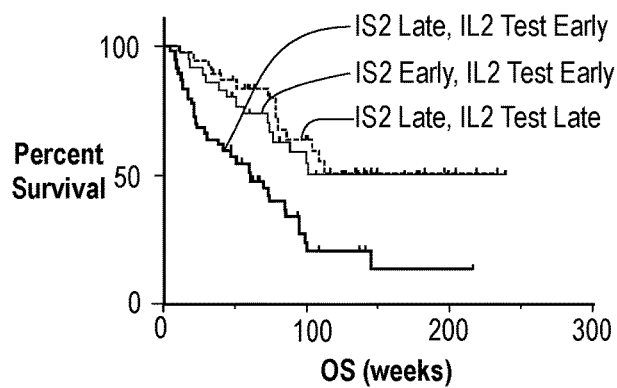

Breaking down by combination of IS2 and IL2 test classifications gives the Kaplan-Meier plots in FIGS. 18A-18B. Both in TTP and OS, outcome is determined by IS2 classification: no patients who are IL2 Test Late have IS2 Early classification and patients who classify as IS2 Late have similar outcome regardless of their IL2 test classification.

Figure 19A:
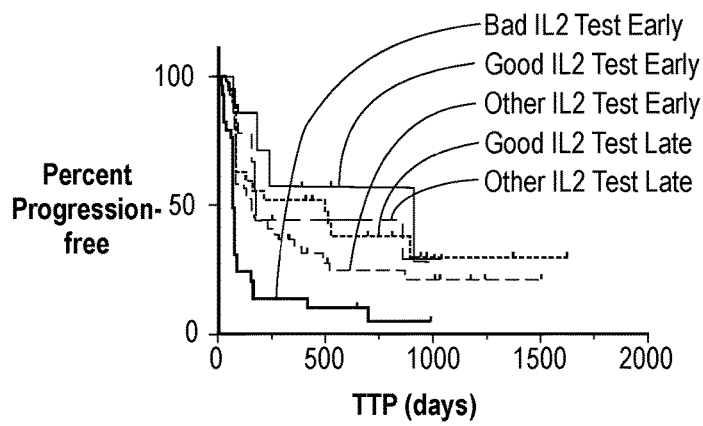
FIGS. 19A and 19B are Kaplan-Meier plots of TTP and OS (FIGS. 19A and 19B, respectively) by combination of the IS6 and IL2 classifiers.
Figure 19B:
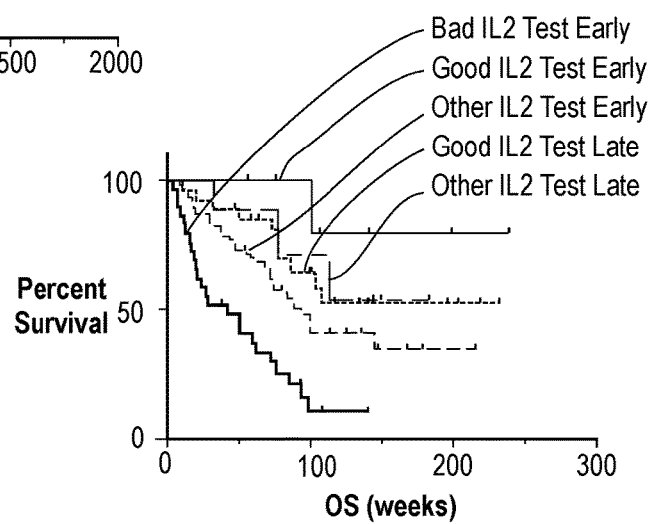

Breaking down by combination of IS6 and IL2 test classifications gives the Kaplan-Meier plots in FIGS. 19A-19B.

Although not quite as clear as for IS2, possibly due to the smaller numbers in some of the subgroups, TTP and OS are determined by IS6 classification: patients who classify as IS6 Good have similar outcome regardless of their IL2 test classification, as do those who classify as IS6 Other. All but one patient classified as IS6 Bad are classified as IL2 test Early and these patients have particularly poor TTP and OS.

Conclusion

These results indicate that the IL2 test is clearly distinct from the IS2 and IS6 tests. There is a group of patients who classify as IL2 test Early and IS2 Early and/or IS6 Bad and these patients have poor outcomes on both therapies (anti-PD-1 and high dose IL2). However, while the IL2 test identifies from the remaining patients a group who do well on IL2 therapy, IS2 and IS6 identify from the remaining patients a group who do well on anti-PD-1 therapy. These groups are not identical, although there are a number of patients who are classified to both good outcome groups.

Additionally, a patient whose sample is classified by the IL2 classifier as Late and the IS6 classifier as Other might be well advised to start with IL2 therapy, but a relatively small percentage of patients fall into this category. There currently exist very little clinical data at all on IL2 administration after checkpoint inhibitors, so getting any good data on sequencing of therapies in both directions (at least IL2 after checkpoint) is challenging at the present but should such data become available the present classifiers may prove very useful since they can predict relative benefit of both IL2 and anti-PD-1 therapies. However, it may still be advantageous and useful to have both IS6 results and IL2 test results available to help make an informed decision about melanoma treatment and general prognosis. For example, if the patient sample is classified by the ILS classifier as Late, they may wish to start therapy with high dose IL2, due to chance of a complete remission and the duration of therapy and side effects, especially if the patient also tested as IS6 Good (and remained that way through the course of IL2 therapy), the patient could take nivolumab later with good chances of a good outcome. This decision would be easier if the patient sample was tested as IS6 Other (or Bad—but this is a very unlikely combination). Conversely, if the patient tested as Early under the IL2 test, the patient may be guided to start with nivolumab.

The appended claims are included as further descriptions of the disclosed inventions.

TABLE 32

Feature Definitions

| Left | Center | Right |
|---|---|---|
| 3071.22 | 3085.19 | 3099.16 |
| 3099.64 | 3111.21 | 3122.77 |
| 3123.96 | 3137.95 | 3151.93 |
| 3192.34 | 3210.69 | 3229.04 |
| 3231.00 | 3243.53 | 3256.07 |
| 3296.71 | 3322.48 | 3348.26 |
| 3348.74 | 3363.68 | 3378.62 |
| 3380.51 | 3393.55 | 3406.59 |
| 3407.82 | 3419.63 | 3431.44 |
| 3434.51 | 3443.90 | 3453.30 |
| 3453.84 | 3465.66 | 3477.47 |
| 3477.78 | 3487.13 | 3496.49 |
| 3497.72 | 3508.15 | 3518.58 |
| 3530.87 | 3553.03 | 3575.20 |
| 3575.55 | 3589.52 | 3603.48 |
| 3603.84 | 3613.47 | 3623.10 |
| 3623.22 | 3636.17 | 3649.13 |
| 3667.09 | 3680.72 | 3694.34 |
| 3694.82 | 3704.05 | 3713.28 |
| 3713.38 | 3723.48 | 3733.58 |
| 3747.77 | 3756.31 | 3764.84 |
| 3766.08 | 3776.17 | 3786.25 |
| 3786.27 | 3795.51 | 3804.76 |
| 3805.44 | 3818.13 | 3830.83 |
| 3832.00 | 3841.64 | 3851.28 |
| 3877.78 | 3888.14 | 3898.49 |
| 3902.63 | 3908.45 | 3914.27 |
| 3915.70 | 3927.75 | 3939.80 |
| 3940.41 | 3952.46 | 3964.50 |
| 3995.34 | 4009.55 | 4023.77 |
| 4039.25 | 4051.40 | 4063.54 |
| 4080.14 | 4094.83 | 4109.53 |
| 4112.17 | 4119.37 | 4126.57 |
| 4127.25 | 4133.39 | 4139.52 |
| 4165.92 | 4170.82 | 4175.73 |
| 4198.95 | 4210.81 | 4222.68 |
| 4243.01 | 4250.23 | 4257.46 |
| 4257.59 | 4265.10 | 4272.62 |
| 4272.87 | 4287.80 | 4302.74 |
| 4329.62 | 4341.78 | 4353.93 |
| 4354.20 | 4361.64 | 4369.08 |
| 4369.23 | 4380.07 | 4390.91 |
| 4392.36 | 4408.98 | 4425.60 |
| 4426.15 | 4433.53 | 4440.90 |
| 4445.65 | 4462.52 | 4479.39 |
| 4500.29 | 4511.57 | 4522.85 |
| 4539.60 | 4546.35 | 4553.09 |
| 4553.30 | 4565.57 | 4577.84 |
| 4578.09 | 4590.49 | 4602.88 |
| 4618.22 | 4625.79 | 4633.36 |
| 4636.26 | 4645.87 | 4655.47 |
| 4667.54 | 4679.28 | 4691.02 |
| 4694.45 | 4714.19 | 4733.92 |
| 4745.60 | 4755.26 | 4764.92 |
| 4766.87 | 4775.61 | 4784.35 |
| 4784.77 | 4792.96 | 4801.15 |
| 4801.90 | 4818.04 | 4834.18 |
| 4836.11 | 4856.83 | 4877.54 |
| 4878.03 | 4892.00 | 4905.97 |
| 4926.11 | 4937.93 | 4949.75 |
| 4950.78 | 4964.54 | 4978.30 |
| 4978.58 | 4985.12 | 4991.65 |
| 4992.26 | 5002.74 | 5013.22 |
| 5014.15 | 5022.47 | 5030.79 |
| 5033.86 | 5044.52 | 5055.18 |
| 5055.82 | 5071.39 | 5086.96 |
| 5092.42 | 5106.90 | 5121.37 |

TABLE 32-continued

Feature Definitions

| Left | Center | Right |
|---|---|---|
| 5121.84 | 5134.31 | 5146.78 |
| 5152.29 | 5158.45 | 5164.61 |
| 5164.71 | 5176.99 | 5189.28 |
| 5211.23 | 5223.66 | 5236.09 |
| 5240.06 | 5251.62 | 5263.18 |
| 5274.29 | 5295.48 | 5316.67 |
| 5351.59 | 5362.36 | 5373.12 |
| 5394.97 | 5416.74 | 5438.51 |
| 5442.72 | 5449.54 | 5456.36 |
| 5511.63 | 5522.35 | 5533.08 |
| 5537.82 | 5549.32 | 5560.82 |
| 5561.13 | 5570.45 | 5579.78 |
| 5618.09 | 5637.53 | 5656.98 |
| 5666.47 | 5674.79 | 5683.10 |
| 5684.19 | 5691.96 | 5699.72 |
| 5699.88 | 5705.55 | 5711.22 |
| 5714.46 | 5720.24 | 5726.02 |
| 5726.03 | 5734.42 | 5742.81 |
| 5744.18 | 5765.03 | 5785.88 |
| 5786.75 | 5794.52 | 5802.30 |
| 5803.89 | 5810.08 | 5816.27 |
| 5816.42 | 5822.76 | 5829.11 |
| 5832.02 | 5840.46 | 5848.89 |
| 5851.99 | 5865.50 | 5879.02 |
| 5879.59 | 5888.74 | 5897.90 |
| 5898.07 | 5909.77 | 5921.47 |
| 5923.79 | 5933.50 | 5943.21 |
| 5943.39 | 5952.76 | 5962.13 |
| 5973.59 | 5985.25 | 5996.91 |
| 5998.01 | 6008.58 | 6019.14 |
| 6019.52 | 6033.18 | 6046.84 |
| 6067.08 | 6081.13 | 6095.18 |
| 6095.91 | 6108.22 | 6120.52 |
| 6120.69 | 6127.36 | 6134.04 |
| 6134.57 | 6148.12 | 6161.67 |
| 6164.40 | 6174.39 | 6184.38 |
| 6186.65 | 6194.45 | 6202.25 |
| 6202.49 | 6209.86 | 6217.23 |
| 6217.50 | 6227.51 | 6237.52 |
| 6275.16 | 6284.15 | 6293.14 |
| 6293.98 | 6303.48 | 6312.97 |
| 6322.56 | 6330.62 | 6338.67 |
| 6338.74 | 6348.00 | 6357.25 |
| 6378.77 | 6393.09 | 6407.42 |
| 6407.61 | 6438.19 | 6468.77 |
| 6470.60 | 6487.32 | 6504.03 |
| 6521.11 | 6534.98 | 6548.85 |
| 6549.49 | 6562.06 | 6574.64 |
| 6575.85 | 6589.26 | 6602.67 |
| 6603.58 | 6652.90 | 6702.22 |
| 6715.26 | 6730.59 | 6745.93 |
| 6798.46 | 6809.11 | 6819.77 |
| 6825.83 | 6837.67 | 6849.52 |
| 6849.89 | 6859.44 | 6868.99 |
| 6869.17 | 6890.30 | 6911.42 |
| 6911.60 | 6920.97 | 6930.34 |
| 6931.26 | 6947.14 | 6963.03 |
| 6963.58 | 6971.11 | 6978.64 |
| 6979.01 | 6995.27 | 7011.52 |
| 7012.07 | 7021.07 | 7030.07 |
| 7030.26 | 7035.12 | 7039.99 |
| 7040.36 | 7053.49 | 7066.62 |
| 7066.99 | 7075.62 | 7084.26 |
| 7118.24 | 7143.95 | 7169.66 |
| 7178.66 | 7189.32 | 7199.97 |
| 7254.70 | 7269.03 | 7283.36 |
| 7283.91 | 7296.95 | 7309.99 |
| 7310.54 | 7341.31 | 7372.07 |
| 7375.19 | 7390.07 | 7404.95 |
| 7405.50 | 7418.63 | 7431.76 |
| 7433.23 | 7447.10 | 7460.97 |
| 7461.04 | 7470.12 | 7479.20 |
| 7479.34 | 7488.35 | 7497.36 |
| 7603.32 | 7617.37 | 7631.42 |
| 7760.24 | 7767.77 | 7775.30 |
| 7775.48 | 7783.32 | 7791.16 |

TABLE 32-continued

Feature Definitions

| Left | Center | Right |
|---|---|---|
| 7803.94 | 7811.50 | 7819.05 |
| 7819.49 | 7828.64 | 7837.80 |
| 7871.88 | 7881.20 | 7890.53 |
| 7984.80 | 7994.91 | 8005.01 |
| 8006.66 | 8018.69 | 8030.72 |
| 8131.01 | 8153.05 | 8175.09 |
| 8192.54 | 8215.68 | 8238.82 |
| 8239.93 | 8254.89 | 8269.86 |
| 8307.15 | 8329.92 | 8352.70 |
| 8353.43 | 8364.46 | 8375.48 |
| 8378.60 | 8391.27 | 8403.95 |
| 8404.18 | 8412.46 | 8420.74 |
| 8420.89 | 8429.89 | 8438.90 |
| 8457.39 | 8464.68 | 8471.97 |
| 8472.01 | 8477.96 | 8483.90 |
| 8484.22 | 8490.81 | 8497.40 |
| 8499.41 | 8508.37 | 8517.33 |
| 8520.60 | 8531.96 | 8543.32 |
| 8555.29 | 8565.12 | 8574.94 |
| 8575.31 | 8592.03 | 8608.74 |
| 8650.07 | 8661.91 | 8673.76 |
| 8716.42 | 8724.60 | 8732.77 |
| 8733.22 | 8742.08 | 8750.93 |
| 8753.20 | 8766.14 | 8779.08 |
| 8800.49 | 8826.76 | 8853.03 |
| 8860.56 | 8871.76 | 8882.96 |
| 8883.70 | 8894.81 | 8905.92 |
| 8906.29 | 8932.10 | 8957.90 |
| 8959.80 | 8969.79 | 8979.78 |
| 8981.37 | 8993.97 | 9006.57 |
| 9007.02 | 9017.58 | 9028.14 |
| 9028.36 | 9038.69 | 9049.02 |
| 9056.50 | 9062.40 | 9068.30 |
| 9068.96 | 9078.57 | 9088.18 |
| 9089.96 | 9098.14 | 9106.31 |
| 9113.47 | 9142.49 | 9171.51 |
| 9196.31 | 9207.88 | 9219.45 |
| 9233.96 | 9244.34 | 9254.72 |
| 9254.90 | 9262.89 | 9270.88 |
| 9271.06 | 9285.48 | 9299.89 |
| 9308.35 | 9319.83 | 9331.31 |
| 9345.77 | 9366.21 | 9386.64 |
| 9387.10 | 9398.69 | 9410.29 |
| 9411.21 | 9454.03 | 9496.84 |
| 9554.47 | 9573.41 | 9592.35 |
| 9613.48 | 9626.56 | 9639.65 |
| 9640.11 | 9654.69 | 9669.27 |
| 9688.55 | 9723.57 | 9758.58 |
| 9759.54 | 9770.54 | 9781.54 |
| 9782.00 | 9792.43 | 9802.87 |
| 9843.02 | 9866.06 | 9889.11 |
| 9900.78 | 9914.98 | 9929.17 |
| 9930.23 | 9949.53 | 9968.83 |
| 9981.27 | 10000.17 | 10019.06 |
| 10067.77 | 10077.87 | 10087.97 |
| 10090.48 | 10098.94 | 10107.40 |
| 10108.11 | 10116.48 | 10124.86 |
| 10126.38 | 10138.78 | 10151.18 |
| 10151.41 | 10161.74 | 10172.07 |
| 10172.76 | 10184.81 | 10196.87 |
| 10200.08 | 10212.14 | 10224.19 |
| 10224.65 | 10236.01 | 10247.38 |
| 10249.52 | 10262.23 | 10274.94 |
| 10276.56 | 10285.67 | 10294.77 |
| 10295.62 | 10305.69 | 10315.75 |
| 10331.12 | 10339.06 | 10346.99 |
| 10351.93 | 10357.22 | 10362.51 |
| 10438.84 | 10449.16 | 10459.47 |
| 10461.23 | 10490.76 | 10520.29 |
| 10520.47 | 10533.16 | 10545.85 |
| 10546.03 | 10557.31 | 10568.60 |
| 10570.41 | 10590.04 | 10609.67 |
| 10615.18 | 10638.37 | 10661.56 |
| 10662.02 | 10684.40 | 10706.79 |
| 10709.31 | 10734.45 | 10759.59 |
| 10761.75 | 10777.84 | 10793.93 |
| 10794.02 | 10804.46 | 10814.89 |
| 10827.64 | 10838.37 | 10849.11 |
| 10851.16 | 10857.90 | 10864.65 |
| 10909.38 | 10922.34 | 10935.29 |
| 10951.44 | 10963.37 | 10975.30 |
| 11028.77 | 11056.40 | 11084.03 |
| 11090.89 | 11107.43 | 11123.96 |
| 11132.45 | 11152.43 | 11172.40 |
| 11285.82 | 11305.10 | 11324.39 |
| 11354.39 | 11366.13 | 11377.86 |
| 11377.88 | 11389.94 | 11401.99 |
| 11402.35 | 11414.43 | 11426.50 |
| 11428.16 | 11442.74 | 11457.32 |
| 11464.41 | 11477.66 | 11490.90 |
| 11491.36 | 11502.31 | 11513.27 |
| 11513.71 | 11530.99 | 11548.26 |
| 11613.00 | 11626.92 | 11640.84 |
| 11643.86 | 11657.11 | 11670.36 |
| 11670.69 | 11686.46 | 11702.22 |
| 11719.74 | 11732.72 | 11745.69 |
| 11746.38 | 11756.13 | 11765.89 |
| 11769.80 | 11786.10 | 11802.40 |
| 11822.14 | 11835.46 | 11848.77 |
| 11867.09 | 11883.39 | 11899.68 |
| 11900.20 | 11913.40 | 11926.61 |
| 11927.82 | 11938.26 | 11948.69 |
| 11949.11 | 11964.95 | 11980.79 |
| 11980.83 | 12004.32 | 12027.80 |
| 12266.86 | 12290.16 | 12313.47 |
| 12436.99 | 12459.03 | 12481.07 |
| 12546.50 | 12573.59 | 12600.69 |
| 12601.37 | 12615.26 | 12629.15 |
| 12661.30 | 12674.73 | 12688.16 |
| 12688.34 | 12697.46 | 12706.58 |
| 12723.06 | 12738.33 | 12753.59 |
| 12769.89 | 12789.06 | 12808.24 |
| 12830.74 | 12870.91 | 12911.09 |
| 12937.95 | 12962.98 | 12988.01 |
| 13049.54 | 13076.86 | 13104.18 |
| 13119.56 | 13135.29 | 13151.02 |
| 13151.61 | 13178.66 | 13205.71 |
| 13259.38 | 13273.73 | 13288.08 |
| 13304.84 | 13325.96 | 13347.09 |
| 13349.01 | 13365.97 | 13382.93 |
| 13403.84 | 13417.46 | 13431.07 |
| 13472.37 | 13490.03 | 13507.68 |
| 13510.31 | 13524.23 | 13538.16 |
| 13558.27 | 13573.12 | 13587.97 |
| 13599.32 | 13613.04 | 13626.75 |
| 13627.85 | 13642.27 | 13656.70 |
| 13700.43 | 13720.06 | 13739.69 |
| 13739.92 | 13781.47 | 13823.03 |
| 13826.35 | 13845.18 | 13864.02 |
| 13864.91 | 13894.51 | 13924.11 |
| 13925.45 | 13942.27 | 13959.08 |
| 13960.63 | 13978.17 | 13995.70 |
| 14024.32 | 14050.51 | 14076.70 |
| 14077.02 | 14099.66 | 14122.31 |
| 14124.55 | 14152.13 | 14179.70 |
| 14180.60 | 14204.59 | 14228.58 |
| 14229.93 | 14254.82 | 14279.70 |
| 14280.60 | 14301.90 | 14323.20 |
| 14412.88 | 14435.30 | 14457.73 |
| 14464.45 | 14489.34 | 14514.23 |
| 14516.47 | 14543.37 | 14570.28 |
| 14571.18 | 14594.72 | 14618.26 |
| 14764.89 | 14786.87 | 14808.84 |
| 14859.96 | 14882.15 | 14904.35 |
| 14951.88 | 14980.13 | 15008.38 |
| 15493.58 | 15509.06 | 15524.53 |
| 15525.61 | 15557.28 | 15588.95 |
| 15611.89 | 15643.05 | 15674.21 |
| 15717.50 | 15751.16 | 15784.83 |
| 16261.72 | 16302.97 | 16344.23 |
| 16447.74 | 16504.38 | 16561.02 |
| 16613.12 | 16657.76 | 16702.40 |

TABLE 32-continued

Feature Definitions

| Left | Center | Right |
|---|---|---|
| 17771.55 | 17809.44 | 17847.33 |
| 17971.11 | 17996.07 | 18021.03 |
| 18021.82 | 18048.07 | 18074.32 |
| 18222.60 | 18264.84 | 18307.08 |
| 18315.44 | 18337.76 | 18360.09 |
| 18360.73 | 18381.93 | 18403.14 |
| 18411.81 | 18440.72 | 18469.63 |
| 18472.84 | 18495.97 | 18519.10 |
| 18542.37 | 18568.09 | 18593.81 |
| 18594.40 | 18638.57 | 18682.74 |
| 18703.22 | 18742.28 | 18781.34 |
| 18811.43 | 18848.65 | 18885.87 |
| 19340.51 | 19374.24 | 19407.97 |
| 19848.35 | 19918.05 | 19987.74 |
| 20754.38 | 20781.06 | 20807.73 |
| 20808.15 | 20831.29 | 20854.43 |
| 20873.86 | 20939.16 | 21004.45 |
| 21006.87 | 21065.87 | 21124.88 |
| 21125.85 | 21173.49 | 21221.13 |
| 21221.61 | 21272.15 | 21322.70 |
| 21323.18 | 21373.24 | 21423.30 |
| 21636.47 | 21786.47 | 21936.48 |
| 21943.18 | 21978.28 | 22013.38 |
| 22991.54 | 23049.38 | 23107.22 |
| 23111.41 | 23130.40 | 23149.38 |
| 23149.78 | 23177.79 | 23205.80 |
| 23205.94 | 23266.87 | 23327.80 |
| 23404.15 | 23469.71 | 23535.26 |
| 24520.14 | 24550.89 | 24581.65 |
| 27895.09 | 27945.61 | 27996.12 |

TABLE 33

Features Used for Classification

| Classifier 1 | Classifier 2 |
|---|---|
| 3085 | 3111 |
| 3244 | 3590 |
| 3444 | 3613 |
| 3842 | 3818 |
| 4590 | 3888 |
| 5158 | 4051 |
| 5177 | 4434 |
| 5570 | 4793 |
| 5720 | 5003 |
| 6589 | 5071 |
| 6809 | 5417 |
| 6890 | 5675 |
| 6995 | 5692 |
| 8478 | 5765 |
| 9208 | 5840 |
| 11913 | 5953 |
| 11938 | 6348 |
| 11965 | 7297 |
| 13781 | 8491 |
| 14543 | 8565 |
| 14595 | 9098 |
| 15509 | 10162 |
|  | 10339 |
|  | 10590 |
|  | 10734 |
|  | 10804 |
|  | 10838 |
|  | 11056 |
|  | 11443 |
|  | 11502 |
|  | 11531 |
|  | 11627 |
|  | 11686 |
|  | 11913 |
|  | 11938 |
|  | 12004 |
| | 12290 |
| | 12459 |
| | 12738 |
| | 12871 |
| | 12963 |
| | 13135 |
| | 13179 |
| | 13326 |
| | 13366 |
| | 13573 |
| | 13642 |
| | 13845 |
| | 14302 |
| | 14543 |
| | 14787 |
| | 18265 |
| | 21173 |
| | 21373 |
| | 23049 |
| | 24551 |

TABLE 34

Classification by Sample

| Sample ID | Classification Label (Classifier 1 + Classifier 2) |
|---|---|
| 4 | Late |
| 5 | Early |
| 23 | Late |
| 24 | Late |
| 30 | Late |
| 32 | Late |
| 33 | Early |
| 36 | Late |
| 37 | Early |
| 38 | Early |
| 39 | Early |
| 40 | Early |
| 41 | Late |
| 59 | Late |
| 60 | Early |
| 61 | Early |
| 62 | Late |
| 63 | Early |
| 64 | Early |
| 65 | Late |
| 66 | Early |
| 67 | Early |
| 68 | Early |
| 69 | Early |
| 70 | Late |
| 71 | Late |
| 72 | Early |
| 73 | Early |
| 74 | Early |
| 75 | Early |
| 76 | Early |
| 77 | Early |
| 78 | Early |
| 79 | Late |
| 80 | Early |
| 81 | Early |
| 82 | Early |
| 83 | Early |
| 84 | Early |
| 85 | Early |
| 86 | Early |
| 87 | Early |
| 88 | Late |
| 89 | Early |
| 90 | Early |

TABLE 34-continued

Classification by Sample

| Sample ID | Classification Label (Classifier 1 + Classifier 2) |
|---|---|
| 91 | Early |
| 93 | Early |
| 94 | Early |
| 95 | Late |
| 96 | Late |
| 97 | Early |
| 98 | Late |
| 100 | Early |
| 101 | Early |
| 102 | Early |
| 103 | Late |
| 105 | Early |
| 106 | Early |
| 107 | Early |
| 108 | Late |
| 109 | Early |
| 111 | Early |
| 112 | Late |
| 113 | Early |
| 114 | Early |
| 116 | Early |
| 118 | Early |
| 119 | Early |
| 120 | Late |
| 122 | Early |
| 123 | Early |
| 124 | Early |
| 125 | Early |
| 126 | Late |
| 127 | Late |
| 128 | Late |
| 129 | Late |
| 130 | Late |
| 131 | Early |
| 132 | Early |
| 133 | Early |
| 134 | Late |
| 135 | Late |
| 136 | Early |
| 137 | Early |
| 138 | Early |
| 140 | Late |
| 141 | Early |
| 142 | Late |
| 143 | Late |
| 144 | Early |
| 145 | Late |
| 146 | Late |
| 147 | Early |
| 149 | Early |
| 150 | Early |
| 151 | Late |
| 152 | Early |
| 153 | Early |
| 154 | Early |
| 156 | Early |
| 157 | Late |
| 158 | Early |
| 160 | Late |
| 161 | Late |
| 162 | Early |
| 163 | Early |
| 164 | Early |
| 165 | Late |
| 166 | Early |
| 167 | Late |
| 168 | Early |
| 169 | Early |
| 170 | Early |

TABLE 35

Proteins included in the extended leading edge set for acute inflammation response (Amigo1). * indicates proteins to the right of the minimum of RS and † indicates proteins with anti-correlations of at least as great magnitude as that at the maximum of RS.

| UniProtID | Protein Name | Correlation | P value |
|---|---|---|---|
| P02741 | C-reactive protein | 0.759 | <0.001 |
| P01024 | Complement C3 | 0.733 | <0.001 |
| P11226 | Mannose-binding protein C | 0.687 | <0.001 |
| P01009 | alpha1-Antitrypsin | 0.585 | 0.005 |
| P01024 | Complement C3a anaphylatoxin | 0.585 | 0.005 |
| P01031 | Complement C5 | 0.585 | 0.005 |
| P07951 | Tropomyosin beta chain | 0.528 | 0.011 |
| Q8NEV9 Q14213 | Interleukin-27 | 0.523 | 0.012 |
| P00738 | Haptoglobin | 0.518 | 0.013 |
| P12956 | ATP-dependent DNA helicase II 70 kDa subunit | 0.515 | 0.013 |
| P33681 | T-lymphocyte activation antigen CD80 | 0.456 | 0.028 |
| P05156 | Complement factor I | 0.446 | 0.032 |
| Q14624 | Inter-alpha-trypsin inhibitor heavy chain H4 | 0.410 | 0.049 |
| Q00535 Q15078 | Cyclin-dependent kinase 5: activator p35 complex | 0.392 | 0.059 |
| P06744 | Glucose phosphate isomerase | 0.385 | 0.065 |
| P02743 | Serum amyloid P | 0.385 | 0.065 |
| P02679 | Fibrinogen gamma chain dimer | 0.379 | 0.068 |
| P01023 | alpha2-Macroglobulin | 0.359 | 0.085 |
| P01024 | Complement C3a anaphylatoxin des Arginine | 0.353 | 0.089 |
| P10600 | Transforming growth factor beta-3 | 0.349 | 0.094 |
| P08107 | Hsp70 | 0.338 | 0.104 |
| P08697 | alpha2-Antiplasmin | −0.826*† | <0.001 |
| P00747 | Angiostatin | −0.518*† | 0.013 |
| P02649 | Apolipoprotein E | −0.421*† | 0.043 |
| Q9BZR6 | Nogo Receptor/reticulon 4 receptor | −0.410*† | 0.049 |
| P02765 | alpha2-HS-Glycoprotein | −0.395*† | 0.058 |
| P08514 P05106 | Integrin alpha-IIb: beta-3 complex | −0.364*† | 0.080 |
| O00626 | Macrophage-derived chemokine | −0.359*† | 0.085 |
| Q9Y5K2 | Kallikrein 4 | −0.326* | 0.118 |

TABLE 36

Proteins included in the extended leading edge set for complement system (Amigo9). † indicates proteins with anti-correlations of at least as great magnitude as that at the maximum of RS.

| UniProtID | Protein Name | Correlation | P value |
|---|---|---|---|
| P02748 | Complement C9 | 0.779 | <0.001 |
| P02741 | C-reactive protein | 0.759 | <0.001 |
| P01024 | Complement C3 | 0.733 | <0.001 |
| P11226 | Mannose-binding protein C | 0.687 | 0.001 |
| P01031 P13671 | Complement C5b, 6 Complex | 0.615 | 0.003 |
| P01024 | Complement C3a anaphylatoxin | 0.585 | 0.005 |
| P01031 | Complement C5 | 0.585 | 0.005 |
| P12956 | ATP-dependent DNA helicase II 70 kDa subunit | 0.515 | 0.013 |
| POC0L4 POC0L5 | Complement C4b | 0.482 | 0.020 |
| P05156 | Complement factor I | 0.446 | 0.032 |
| P13671 | Complement C6 | 0.426 | 0.041 |
| P02743 | Serum amyloid P | 0.385 | 0.065 |
| P05155 | C1-Esterase Inhibitor | 0.374 | 0.072 |
| P01023 | alpha2-Macroglobulin | 0.359 | 0.085 |
| P09871 | Complement C1s | 0.359 | 0.085 |
| P01024 | Complement C3a anaphylatoxin des Arginine | 0.354 | 0.089 |
| P00736 | Complement C1r | 0.297 | 0.154 |
| P10643 | Complement C7 | 0.292 | 0.161 |

TABLE 36-continued

Proteins included in the extended leading edge set for complement system (Amigo9). † indicates proteins with anti-correlations of at least as great magnitude as that at the maximum of RS.

| UniProtID | Protein Name | Correlation | P value |
|---|---|---|---|
| P01024 | Complement C3b | 0.287 | 0.169 |
| P01031 | Complement C5a | 0.287 | 0.169 |
| Q15848 | Adiponectin | 0.287 | 0.169 |
| P07357 P07358 P07360 | Complement C8 | 0.272 | 0.193 |
| P00746 | Complement factor D | 0.262 | 0.210 |
| P16109 | P-Selectin | −0.451† | 0.030 |
| P16581 | E-Selectin | −0.292† | 0.161 |
| O75636 | Ficolin-3 | −0.262† | 0.210 |

TABLE 37

Proteins included in the extended leading edge set for wound healing (Amigo16). * indicates proteins to the left of the maximum of RS and † indicates proteins with anti-correlations of at least as great magnitude as that at the minimum of RS.

| UniProtID | Protein Name | Correlation | P value |
|---|---|---|---|
| P08697 | alpha2-Antiplasmin | −0.826 | <0.001 |
| P03952 | Prekallikrein | −0.666 | 0.001 |
| P04196 | Histidine-proline-rich glycoprotein | −0.579 | 0.005 |
| P07359 | Platelet Glycoprotein Ib alpha | −0.533 | 0.010 |
| P06396 | Gelsolin | −0.528 | 0.011 |
| P00747 | Angiostatin | −0.518 | 0.013 |
| P07996 | Thrombospondin-1 | −0.508 | 0.015 |
| P00747 | Plasminogen | −0.503 | 0.016 |
| P02649 | Apolipoprotein E (isoform E2) | −0.431 | 0.038 |
| P02649 | Apolipoprotein E | −0.421 | 0.043 |
| P53582 | Methionine aminopeptidase 1 | −0.405 | 0.051 |
| P02649 | Apolipoprotein E3 | −0.400 | 0.055 |
| P02649 | Apolipoprotein E4 | −0.400 | 0.055 |
| P37023 | Activin receptor-like kinase 1 | 0.467*† | 0.025 |
| P02671 P02675 P02679 | Fibrinogen | 0.456*† | 0.028 |
| P02679 | Fibrinogen gamma chain dimer | 0.379* | 0.068 |
| P02671 P02675 P02679 | D-dimer | 0.364* | 0.080 |

TABLE 38

Proteins included in the extended leading edge set for acute phase (UNIPROT1). * indicates proteins to the right of the minimum of RS and † indicates proteins with anti-correlations of at least as great magnitude as that at the maximum of RS.

| UniProtID | Protein Name | Correlation | P value |
|---|---|---|---|
| P02741 | C-reactive protein | 0.759 | <0.001 |
| P11226 | Mannose-binding protein C | 0.687 | 0.001 |
| P01009 | alpha1-Antitrypsin | 0.585 | 0.005 |
| P00738 | Haptoglobin | 0.518 | 0.013 |
| P0DJI8 | Serum amyloid A | 0.513 | 0.014 |
| P18428 | Lipopolysaccharide-binding protein | 0.482 | 0.020 |
| Q14624 | Inter-alpha-trypsin inhibitor heavy chain H4 | 0.410 | 0.049 |
| P02743 | Serum amyloid P | 0.385 | 0.065 |
| P02671 P02675 P02679 | D-dimer | 0.364 | 0.080 |
| P01023 | alpha2-Macroglobulin | 0.359 | 0.085 |
| P08697 | alpha2-Antiplasmin | −0.826*† | <0.001 |
| P02765 | alpha2-HS-Glycoprotein | −0.395† | 0.058 |

We claim:

1. A method for predicting whether a melanoma patient is likely to benefit from high dose IL2 therapy, comprising the steps of:
    a) performing, by a mass spectrometer, mass spectrometry on a blood-based sample of the patient and obtaining mass spectrometry data of the sample;
    b) performing, by a computer implementing a classifier, a classification of the mass spectrometry data obtained by the mass spectrometer, wherein the classifier is developed from a development set of samples from melanoma patients treated with the high dose IL2 therapy comprising:
    iteratively training, by the computer, Classifier 1 from the development set of samples and a set of mass spectral features identified as being associated with an acute response biological function to generate an Early class label, a Late class label, or the equivalent for each of a subset of samples, and
    iteratively training, by the computer, Classifier 2 from a subset of samples classified with the Late class label by Classifier 1 in the development set of samples to generate an Early class label, a Late class label or the equivalent,
    c) supplying, from the computer to a programmed computer trained to predict whether the melanoma patient is likely to benefit from treatment with high dose IL2 therapy, the mass spectrometry data of the sample obtained in step a) to a classifier using Classifier 1 and Classifier 2, wherein:
    the classifier represents a k-nearest neighbor (kNN) classification algorithm implemented by the programmed computer and is arranged as a hierarchical combination of (a) the Classifier 1 classifying the patient into either a first Late group or a first Early group or the equivalent, and (b) the Classifier 2 further classifying the first Late group into a second Late group or a second Early group, wherein the patient classified into the first Late group or the second Late group is predicted to be likely to benefit from high dose IL2 therapy,
    d) determining a Late class label for the sample from Classifier 2; and
    e) administering the high dose IL2 therapy responsive to determining the Late class label for the sample.

2. The method of claim 1, wherein Classifier 1 and Classifier 2 use features for performing classification of the sample or a subset thereof as follows:

| Classifier 1 | Classifier 2 |
|---|---|
| 3085 | 3111 |
| 3244 | 3590 |
| 3444 | 3613 |
| 3842 | 3818 |
| 4590 | 3888 |
| 5158 | 4051 |
| 5177 | 4434 |
| 5570 | 4793 |
| 5720 | 5003 |
| 6589 | 5071 |
| 6809 | 5417 |
| 6890 | 5675 |
| 6995 | 5692 |
| 8478 | 5765 |
| 9208 | 5840 |
| 11913 | 5953 |
| 11938 | 6348 |
| 11965 | 7297 |
| 13781 | 8491 |
| 14543 | 8565 |
| 14595 | 9098 |
| 15509 | 10162 |
|  | 10339 |

-continued

| Classifier 1 | Classifier 2 |
|---|---|
| | 10590 |
| | 10734 |
| | 10804 |
| | 10838 |
| | 11056 |
| | 11443 |
| | 11502 |
| | 11531 |
| | 11627 |
| | 11686 |
| | 11913 |
| | 11938 |
| | 12004 |
| | 12290 |
| | 12459 |
| | 12738 |
| | 12871 |
| | 12963 |
| | 13135 |
| | 13179 |
| | 13326 |
| | 13366 |
| | 13573 |
| | 13642 |
| | 13845 |
| | 14302 |
| | 14543 |
| | 14787 |
| | 18265 |
| | 21173 |
| | 21373 |
| | 23049 |
| | 24551. |

3. A method of detecting class labels for a melanoma patient comprising performing the method of claim 1, as well as classifying the sample of the patient with a classifier developed from mass spectral data of a set of blood based samples obtained from melanoma patients treated with an anti-PD-1 drug to generate a class label, wherein class labels are detected.

4. A method of detecting a class label for a melanoma patient on high dose IL2 therapy by performing, by a mass spectrometer, mass spectrometry on a blood based sample from the melanoma patient and obtaining, at a computer implementing a classifier, mass spectrometry data of the sample; performing a classification of the mass spectrometry data using the computer implementing the classifier, wherein the classifier is developed from a development set of blood based samples obtained from melanoma patients treated with an anti-PD-1 drug, comprising iteratively training the classifier from the development set of samples to generate a class label of Late or the equivalent and Early or the equivalent, supplying, from the computer implementing the classifier to a programmed computer trained to predict whether a melanoma patient is likely to benefit from treatment with the anti-PD-1 drug, the mass spectrometry data of the blood based sample from the melanoma patient to the classifier, wherein the patient having a class label of Late or the equivalent is predicted to be likely to benefit from the anti-PD-1 drug, determining the class label of Late or the equivalent for the sample using the classifier, and administering the anti-PD-1 drug responsive to determining the class label of Late of the equivalent for the sample.

* * * * *